US007226942B2

(12) United States Patent
Sher et al.

(10) Patent No.: US 7,226,942 B2
(45) Date of Patent: *Jun. 5, 2007

(54) 2-AMINO-4-FUNCTIONALIZED TETRALIN DERIVATIVES AND RELATED GLYCOGEN PHOSPHORYLASE INHIBITORS

(75) Inventors: Philip M. Sher, Plainsboro, NJ (US); Alexandra A. Nirschl, Yardley, PA (US); Wei Meng, Pennington, NJ (US); William N. Washburn, Titusville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/272,845

(22) Filed: Nov. 14, 2005

(65) Prior Publication Data
US 2006/0111338 A1 May 25, 2006

Related U.S. Application Data

(60) Provisional application No. 60/628,063, filed on Nov. 15, 2004.

(51) Int. Cl.
A61K 31/404 (2006.01)
A61K 31/405 (2006.01)
A61K 31/4709 (2006.01)
C07D 209/12 (2006.01)
C07D 209/14 (2006.01)
C07D 215/38 (2006.01)
C07D 401/12 (2006.01)

(52) U.S. Cl. .................. 514/419; 514/423; 514/314; 514/414; 546/161; 548/454; 548/492; 548/506; 548/510; 548/516

(58) Field of Classification Search ................ 514/419, 514/423; 548/492, 506, 516, 510
See application file for complete search history.

(56) References Cited

U.S. PATENT DOCUMENTS

| 5,952,322 | A | 9/1999 | Hoover et al. | |
|---|---|---|---|---|
| 5,998,463 | A | 12/1999 | Hulin et al. | |
| 6,589,970 | B2 | 7/2003 | Commons et al. | |
| 2001/0046958 | A1 | 11/2001 | Treadway | |
| 2003/0073731 | A1 | 4/2003 | Lee | |
| 2004/0002495 | A1 | 1/2004 | Sher et al. | |
| 2006/0111413 | A1* | 5/2006 | Sher et al. ................ | 514/394 |
| 2006/0111414 | A1* | 5/2006 | Wu et al. ................... | 514/394 |

FOREIGN PATENT DOCUMENTS

| EP | 0 624 575 | 11/1994 | |
|---|---|---|---|
| EP | 978 279 | 2/2000 | |
| EP | 1 041 068 | 10/2000 | |
| EP | 1 149 580 | 1/2001 | |
| EP | 1 088 824 | 4/2001 | ................ 495/4 |
| EP | 1 136 071 | 9/2001 | |
| EP | 1 177 791 | 2/2002 | |
| JP | 9-100278 | 4/1997 | |
| JP | 2004-196702 | 7/2004 | |
| WO | WO 96/39384 | 12/1996 | |
| WO | WO 96/39385 | 12/1996 | |
| WO | WO 99/26659 | 6/1999 | |
| WO | WO 99/43663 | 9/1999 | |
| WO | WO 00/15645 | 3/2000 | |
| WO | WO 00/47206 | 8/2000 | |
| WO | WO 01/23347 | 4/2001 | |
| WO | WO 01/32622 | 5/2001 | |
| WO | WO 02/20530 | 3/2002 | |
| WO | WO 02/064546 | 8/2002 | |
| WO | WO 02/064565 | 8/2002 | |
| WO | WO 03/035621 | 5/2003 | |
| WO | WO 03/037864 | 5/2003 | ................ 209/42 |

(Continued)

OTHER PUBLICATIONS

Co-pending U.S. Appl. No. 11/273,167, filed Nov. 14, 2005.

(Continued)

Primary Examiner—Kamal A. Saeed
Assistant Examiner—Yong Chu
(74) Attorney, Agent, or Firm—Terence J. Bogie

(57) ABSTRACT

Novel compounds are provided which are glycogen phosphorylase inhibitors which are useful in treating, preventing or slowing the progression of diseases requiring glycogen phosphorylase inhibitor therapy such as diabetes and related conditions (such as hyperglycemia, impaired glucose tolerance, insulin resistance and hyperinsulinemia), the microvascular complications associated with diabetes (such as retinopathy, neuropathy, nephropathy and delayed wound healing), the macrovascular complications associated with diabetes (cardiovascular diseases such as atherosclerosis, abnormal heart function, myocardial ischemia and stroke), as well as Metabolic Syndrome and its component conditions including hypertension, obesity and dislipidemia (including hypertriglyceridemia, hypercholesterolemia and low HDL), and other maladies such as non-cardiac ischemia, infection and cancer. These novel compounds have the structure

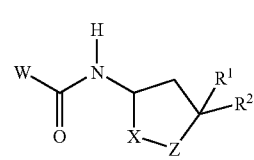

I or stereoisomers or prodrugs or pharmaceutically acceptable salts thereof, wherein W, $R^1$, $R^2$, X and Z are defined herein.

7 Claims, No Drawings

FOREIGN PATENT DOCUMENTS

| | | | | |
|---|---|---|---|---|
| WO | WO 03/072570 | 9/2003 | ................ | 405/12 |
| WO | WO 03/074484 | 9/2003 | | |
| WO | WO 03/074513 | 9/2003 | ................ | 401/12 |
| WO | WO 03/074531 | 9/2003 | | |
| WO | WO 03/074532 | 9/2003 | ................ | 495/4 |
| WO | WO 03/091213 | 11/2003 | | |
| WO | WO 03/104188 | 12/2003 | | |
| WO | WO 04/041780 | 5/2004 | | |
| WO | WO 04/072060 | 8/2004 | | |
| WO | WO 04/078743 | 9/2004 | | |

OTHER PUBLICATIONS

Co-pending U.S. Appl. No. 11/273,445, filed Nov. 14, 2005.
Co-pending U.S. Appl. No. 11/273,479, filed Nov. 14, 2005.
Proc. Natl. Acad. Sci. USA 1998, 95, 1776-1781.
J. Med. Chem. 1998, 41, 2934-2938.
Exp. Opin. Invest. Drugs 2001, 10, 439-454.
J. Med. Chem. 2002, 45, 1002-1018.
Journal of Pharmaceutical Sciences, vol. 64(6), 1975, 1001-1005.

* cited by examiner

2-AMINO-4-FUNCTIONALIZED TETRALIN DERIVATIVES AND RELATED GLYCOGEN PHOSPHORYLASE INHIBITORS

This application claims the benefit of U.S. Provisional Application No. 60/628,063, filed Nov. 15, 2004, incorporated herein by reference in its entirety.

BACKGROUND OF THE INVENTION

Approximately 100 million people worldwide suffer from type II diabetes, which is typically characterized by hyperglycemia due to excessive hepatic glucose production and peripheral insulin resistance, the root causes for which are as yet unknown. Hyperglycemia is considered to be the major risk factor for the development of diabetic complications, such as retinopathy, neuropathy, nephropathy and macrovascular disease.

Accordingly, hepatic glucose production is an important potential target for type II diabetes therapy. The liver produces glucose by glycogenolysis (breakdown of the glucose polymer glycogen) and gluconeogenesis (synthesis of glucose from 2- and 3-carbon precursors). Particularly, glycogenolysis is catalyzed in the liver, muscle and brain by tissue-specific isoforms of the enzyme glycogen phosphorylase. Prior studies suggest that glycogenolysis may make an important contribution to hepatic glucose output in type II diabetes. See, for example, WO 96/39384; WO 96/39385; EP 978279; Proc. Natl. Acad. Sci. USA 1998, 95, 1776–1781; J. Med. Chem. 1998, 41, 2934–2938; Exp. Opin. Invest. Drugs 2001, 10, 439–454; EP 1136071; and WO 03/37864. Thus, glycogen phosphorylase inhibitors are believed to be useful therapeutic agents for treating type II diabetes and delaying the onset of diabetic complications by decreasing hepatic glucose production and lowering glycemia, while providing minimal risk of hypoglycemia and weight gain. See Id.

Based on the aforementioned references and additional references, for example, WO 96/39384; WO 96/39385; WO 00/47206; U.S. Pat. No. 5,952,322; WO 99/43663; EP 1088824; US 2001/0046958; EP 1149580; WO 01/23347; EP 1177791; WO 99/26659; U.S. Pat. No. 5,998,463; EP 1136071; US 2004/0002495 and EP 1041068, it is believed that glycogen phosphorylase inhibitors may be useful in treating, preventing or slowing the progression of diseases such as diabetes and related conditions (such as hyperglycemia, impaired glucose tolerance, insulin resistance and hyperinsulinemia), the microvascular complications associated with diabetes (such as retinopathy, neuropathy, nephropathy and delayed wound healing), the macrovascular complications associated with diabetes (cardiovascular diseases such as atherosclerosis, abnormal heart function, myocardial ischemia and stroke), as well as Metabolic Syndrome and its component conditions including hypertension, obesity and dislipidemia (including hypertriglyceridemia, hypercholesterolemia and low HDL), and other maladies such as non-cardiac ischemia, infection and cancer.

SUMMARY OF THE INVENTION

In accordance with the present invention, 2-amino-4-functionalized tetralin and related compounds are provided that have the general structure of formula I:

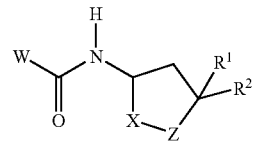

wherein W, $R^1$, $R^2$, X and Z are defined below.

The compounds of the present invention inhibit the activity of the enzyme glycogen phosphorylase. Consequently, the compounds of the present invention may be used in the treatment of multiple diseases or disorders associated with glycogen phosphorylase activity, such as diabetes and related conditions (such as hyperglycemia, impaired glucose tolerance, insulin resistance and hyperinsulinemia), the microvascular complications associated with diabetes (such as retinopathy, neuropathy, nephropathy and delayed wound healing), the macrovascular complications associated with diabetes (cardiovascular diseases such as atherosclerosis, abnormal heart function, myocardial ischemia and stroke), as well as Metabolic Syndrome and its component conditions including hypertension, obesity and dislipidemia (including hypertriglyceridemia, hypercholesterolemia and low HDL), and other maladies such as non-cardiac ischemia, infection and cancer.

Inhibitors of the glycogen phosphorylase enzyme are also described in U.S. patent applications Ser. Nos. 11/273,167, 11/273,445, and 11/273,479, titled "2-Amino-3-Functionalized Tetralin Derivatives and Related Glycogen Phosphorylase Inhibitors", "2-Amino-1-Functionalized Tetralin Derivatives and Related Glycogen Phosphorylase Inhibitors" and "2-Aminonaphthalene Derivatives and Related Glycogen Phosphorylase Inhibitors", respectively, having the same assignee as the present invention and filed concomitantly herewith.

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further, in accordance with the present invention, a method is provided for preventing, inhibiting or treating the progression or onset of diseases or disorders associated with the activity of the enzyme glycogen phosphorylase, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

DETAILED DESCRIPTION OF THE INVENTION

In one embodiment, the present invention discloses novel compounds of formula I:

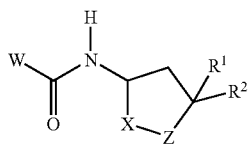

or stereoisomers or prodrugs or pharmaceutically acceptable salts thereof, wherein:

W is a bicyclic heteroaryl of the structure

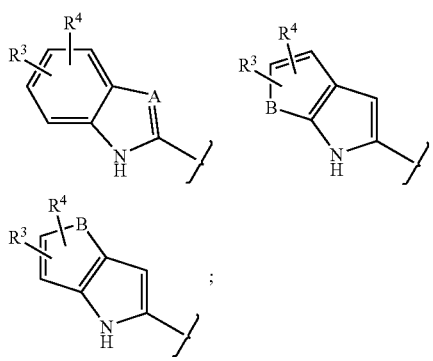

X is —CH$_2$—, —CH$_2$CH$_2$— or —CH$_2$O— (wherein oxygen is bonded to Z);

Z is an aryl or heteroaryl group of the following structure:

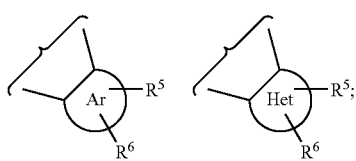

A is —CH— or —N—;

B is —O— or —S—;

R$^1$ and R$^2$ are each independently hydrogen, alkyl, aryl, arylalkyl, heteroarylalkyl, alkenyl, OR$^{7A}$, OCO$_2$R$^8$, OCONR$^{7A}$R$^{7B}$, CN, CN$_4$R$^{7A}$ (tetrazole), CO$_2$R$^{7A}$, CONR$^{7A}$R$^{7B}$, CONR$^{7A}$OR$^{7B}$, NR$^{7A}$COCO$_2$R$^{7B}$ or another hydrogen bonding group, or R$^1$ and R$^2$ are together oxo (=O), =NOR$^{7A}$ or alkylidenyl, any of which may be optionally substituted with a hydrogen bonding group, and provided that R$^1$ and R$^2$ are not both hydrogen or hydroxy;

R$^3$ and R$^4$ are each independently hydrogen, halo, trifluoromethyl, cyano, alkyl or alkoxy;

R$^5$ and R$^6$ are each independently hydrogen, halo, trifluoromethyl, cyano, hydroxy, another hydrogen bonding group, alkyl, aryl, arylalkyl, heteroarylalkyl, alkoxy, aryloxy or alkenyl;

R$^{7A}$ and R$^{7B}$ are independently hydrogen, alkyl, arylalkyl, heteroarylalkyl or aryl, or R$^{7A}$ and R$^{7B}$ may optionally be cyclized together to form a ring, wherein said ring may further be substituted with one to three additional hydrogen bonding groups;

R$^8$ is alkyl, aryl, arylalkyl or heteroarylalkyl; and wherein when R$^1$, R$^2$, R$^5$ and R$^6$ are alkyl, aryl, arylalkyl, heteroarylalkyl, alkenyl, alkoxy or aryloxy, R$^1$, R$^2$, R$^5$ and R$^6$ may each independently be substituted with one to three hydrogen bonding groups.

Some preferred compounds are those in which W is:

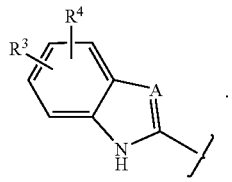

Some more preferred compounds are those in which A is CH.

Some preferred compounds are those in which:

Z is an aryl or heteroaryl group of the structure

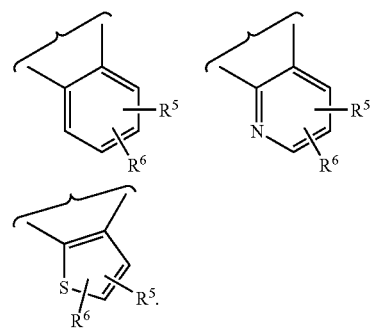

Some additional preferred compounds of the present invention are those in which:

the hydrogen bonding group is preferably selected from the set of monovalent hydrogen bonding groups consisting of OR$^{7A}$, OCO$_2$R$^8$, OCONR$^{7A}$R$^{7B}$, CN, NO$_2$, CN$^4$R$^{7A}$ (tetrazole), COCF$_3$, COR$^{7A}$, CO$_2$R$^{7A}$, CONR$^{7A}$R$^{7B}$, CONR$^{7A}$OR$^{7B}$, C(NR$^{7A}$)NR$^{7B}$R$^{7C}$, CONR$^{7A}$SO$_2$R$^{7B}$, SOR$^8$, SO$_2$R$^8$, SO$_3$H, SO$_2$NR$^{7A}$R$^{7B}$, SO$_2$NR$^{7A}$COR$^{7B}$, SO$_2$NR$^{7A}$CONR$^{7B}$R$^{7C}$, POR$^{7A}$R$^{7B}$, PO$_2$R$^{7A}$R$^{7B}$, PO$_3$R$^{7A}$R$^{7B}$, PO$_2$R$^{7A}$NR$^{7B}$R$^{7C}$, NR$^{7A}$R$^{7B}$, NR$^{7A}$COR$^{7B}$, NR$^{7A}$C(NR$^{7B}$)R$^{7C}$, NR$^{7A}$CO$_2$R$^8$, NR$^{7A}$COCO$_2$R$^{7B}$, NR$^{7A}$CONR$^{7B}$R$^{7C}$, NR$^{7A}$C(NR$^{7B}$)NR$^{7C}$R$^{7D}$, NR$^{7A}$ SO$_2$R$^{7B}$, NR$^{7A}$CONR$^{7B}$SO$_2$R$^{7C}$, NR$^{7A}$SO$_2$NR$^{7B}$R$^{7C}$, NR$^{7A}$POR$^{7B}$R$^{7C}$, NR$^{7A}$PO$_2$R$^{7B}$R$^{7C}$, NR$^{7A}$PO$_3$R$^{7B}$R$^{7C}$ and NR$^{7A}$PO$_2$R$^{7B}$NR$^{7C}$R$^{7D}$, or the set of divalent hydrogen bonding groups consisting of —O—, —CO—, —SO$_2$—, —NR$^{7A}$—, —CO$_2$—, —CONR$^{7A}$—, —SO$_2$NR$^{7A}$—, —OCONR$^{7A}$—, —NR$^{7A}$CONR$^{7B}$—, —N(COR$^{7A}$)—, —N(CO$_2$R$^{7A}$)—, —N(CONR$^{7A}$R$^{7B}$)— and —N(SO$_2$NR$^{7A}$R$^{7B}$)—;

wherein

R$^{7C}$ and R$^{7D}$ are each independently hydrogen, alkyl, arylalkyl, heteroarylalkyl or aryl; and wherein R$^{7A}$, R$^{7B}$, R$^{7C}$, R$^{7D}$ or R$^8$ may further be substituted with one to three additional hydrogen bonding groups;

and wherein
two of $R^{7A}$, $R^{7B}$, $R^{7C}$ or $R^{7D}$ within the same hydrogen bonding group may optionally be cyclized together to form a ring, wherein said ring may further be substituted with one to three additional hydrogen bonding groups.

Preferred compounds also include those compounds in which:
at least one of $R^1$ and $R^2$ is substituted alkyl, $OR^{7A}$, $OCONR^{7A}R^{7B}$, CN, $CN_4R$ (tetrazole), $CO_2R^{7A}$, $CONR^{7A}R^{7B}$ or $NR^{7A}COCO_2R^{7B}$;
$R^{7A}$ and $R^{7B}$ are hydrogen or alkyl;
X is —$CH_2$—;
W is

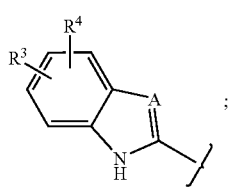

and Z is

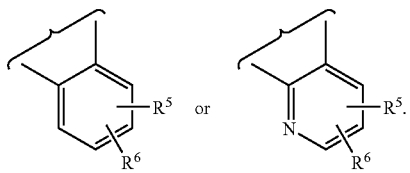

Some particularly preferred compounds are those in which W is 5-chloroindol-2-yl.

Some more particularly preferred compounds are those in which the compound is selected from the compounds of Table 1.

In another embodiment, the present invention relates to pharmaceutical compositions comprised of a therapeutically effective amount of a compound of the present invention, alone or, optionally, in combination with a pharmaceutically acceptable carrier and/or one or more other agent(s). The preferred, particularly preferred, and more particularly preferred compounds set forth above can be used in this embodiment.

In another embodiment, the present invention relates to methods of inhibiting the activity of the enzyme glycogen phosphorylase comprising administering to a mammalian patient, preferably a human patient, in need thereof a therapeutically effective amount of a compound of the present invention, alone or, optionally, in combination with another compound of the present invention and/or at least one other type of therapeutic agent. The preferred, particularly preferred, and more particularly preferred compounds set forth above can be used in this embodiment.

In another embodiment, the present invention relates to a method for preventing, inhibiting or treating the progression or onset of diseases or disorders associated with the activity of the enzyme glycogen phosphorylase comprising administering to a mammalian patient, preferably a human patient, in need of prevention, inhibition or treatment a therapeutically effective amount of a compound of the present invention, alone, or, optionally, in combination with another compound of the present invention and/or at least one other type of therapeutic agent. The preferred, particularly preferred, and more particularly preferred compounds set forth above can be used in this embodiment.

Examples of diseases or disorders associated with the activity of the enzyme glycogen phosphorylase that can be prevented, inhibited, or treated according to the present invention include, but are not limited to, diabetes and related conditions (such as hyperglycemia, impaired glucose tolerance, insulin resistance and hyperinsulinemia), the microvascular complications associated with diabetes (such as retinopathy, neuropathy, nephropathy and delayed wound healing), the macrovascular complications associated with diabetes (cardiovascular diseases such as atherosclerosis, abnormal heart function, myocardial ischemia and stroke), as well as Metabolic Syndrome and its component conditions including hypertension, obesity and dislipidemia (including hypertriglyceridemia, hypercholesterolemia and low HDL), and other maladies such as non-cardiac ischemia, infection and cancer.

Definitions

The following abbreviations have the indicated meanings:
min=minute(s)
h or hr=hour(s)
L=liter(s)
mL=milliliter(s)
µ=microliter(s)
g=gram(s)
mg=milligram(s)
mol=mole(s)
M=molar
mmol=millimole(s)
HPLC=high performance liquid chromatography
HPLC/MS or LC/MS=high performance liquid chromatography/mass spectrometry
MS or Mass Spec=mass spectrometry
[M+H]$^+$=parent plus a proton
[M−H]$^-$=parent minus a proton The following definitions apply to the terms as used throughout this specification, unless otherwise limited in specific instances.

The term "hydrogen bonding group(s)" describes functional groups that may form a hydrogen bond by either donating or accepting a hydrogen atom. Examples of suitable "hydrogen bonding group(s)" include, but are not limited to the monovalent groups $OR^{7A}$, $OCO_2R^8$, $OCONR^{7A}R^{7B}$, CN, $NO_2$, $CN_4R^{7A}$ (tetrazole), $COCF_3$, $COR^{7A}$, $CO_2R^{7A}$, $CONR^{7A}R^{7B}$, $CONR^{7A}OR^{7B}$, $C(NR^{7A})NR^{7B}R^{7C}$, $CONR^{7A}SO_2R^{7B}$, $SOR^8$, $SO_2R^8$, $SO_3H$, $SO_2NR^{7A}R^{7B}$, $SO_2NR^{7A}COR^{7B}$, $SO_2NR^{7A}CONR^{7B}R^{7C}$, $POR^{7A}R^{7B}$, $PO_2R^{7A}R^{7B}$, $PO_3R^{7A}R^{7B}$, $PO_2R^{7A}NR^{7B}R^{7C}$, $NR^{7A}R^{7B}$, $NR^{7A}COR^{7B}$, $NR^{7A}C(NR^{7B})R^{7C}$, $NR^{7A}CO_2R^8$, $NR^{7A}COCO_2R^{7B}$, $NR^{7A}CONR^{7B}R^{7C}$, $NR^{7A}C(NR^{7B})NR^{7C}R^{7D}$, $NR^{7A}SO_2R^{7B}$, $NR^{7A}CONR^{7B}SO_2R^{7C}$, $NR^{7A}SO_2NR^{7B}R^{7C}$, $NR^{7A}POR^{7B}R^{7C}$, $NR^{7A}PO_2R^{7B}R^{7C}$, $NR^{7A}PO_3R^{7B}R^{7C}$ and $NR^{7A}PO_2R^{7B}NR^{7C}R^{7D}$, and the divalent groups —O—, —CO—, —$SO_2$—, —$NR^{7A}$—, —$CO_2$—, —$CONR^{7A}$—, —$SO_2NR^{7A}$—, —$OCONR^{7A}$—, —$NR^{7A}CONR^{7B}$—, —$N(COR^{7A})$—, —$N(CO_2R^{7A})$—, —$N(CONR^{7A}R^{7B})$— and —$N(SO_2NR^{7A}R^{7B})$—, and the like, wherein
$R^{7A}$, $R^{7B}$, $R^{7C}$ and $R^{7D}$ for each occurrence are each independently hydrogen, alkyl, arylalkyl, heteroarylalkyl or aryl; and
$R^8$ is alkyl, arylalkyl, heteroarylalkyl, or aryl.

Moreover, $R^{7A-7D}$ and $R^8$ may be further substituted with one to three hydrogen bonding groups. For example, by substitution with the monovalent hydrogen bonding group OH, $CONR^{7A}R^{7B}$ may represent $CON(Me)CH_2CH_2OH$. Optionally, two of $R^{7A}$, $R^{7B}$, $R^{7C}$ or $R^{7D}$ within the same hydrogen bonding group may be cyclized together to form a ring by joining the two R groups with either a bond or with a divalent hydrogen bonding group. For example, $CONR^{7A}R^{7B}$ may represent $CON(CH_2CH_2CH_2CH_2)$, N-acylated pyrrolidine, or $CON(CH_2CH_2NHCH_2CH_2)$, N-acylated piperidine. Said ring may further be substituted with one to three additional hydrogen bonding groups, for example N-acylated hydroxyproline or N-acylated 3,4-dihydroxypyrrolidine.

In addition, when an R group is itself equal to a hydrogen bonding group, said hydrogen bonding group is a monovalent hydrogen bonding group. However, when an R group is substituted with a hydrogen bonding group, said hydrogen bonding group may be either a monovalent or a divalent hydrogen bonding group.

Substitution of any single R group with a divalent hydrogen bonding group preferably forms a ring. For example, substitution of a 2-butyl group at the 1- and 4-positions with —O— forms a 3-tetrahydrofuranyl group. Substitution of a 1-pentyl group at the 1- and 5-positions with —CO— forms a 2-oxocyclohexyl group.

The term "alkyl" as employed herein, alone or as part of another group, includes straight chain, branched chain and saturated cyclic hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, cyclopropyl, cyclohexyl, and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, that include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl.

Unless otherwise indicated, the term "alkylidenyl" as used herein by itself or as part of another group refers to straight or branched chain geminally divalent radicals of 2 to 20 carbons, preferably 2 to 12 carbons, and more preferably 2 to 8 carbons in the normal chain, that are attached via a double bond, such as methylidenyl, isopropylidenyl, pentylidenyl, and the like.

Unless otherwise indicated, the term "aryl" or "Ar" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one additional fused heterocyclic ring, for example:

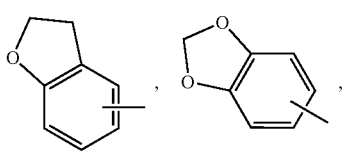

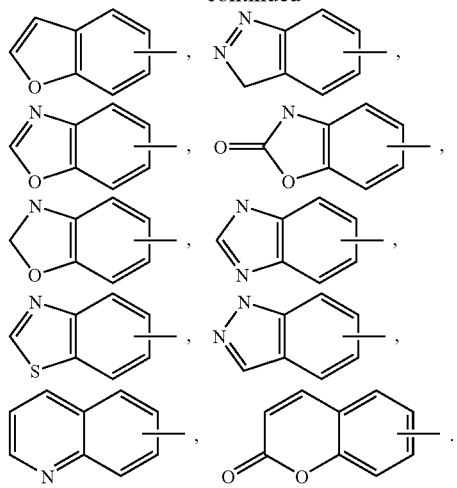

Aryl groups as defined above may optionally be substituted with alkyl groups containing up to six carbons and/or with halogen groups.

The term "arylalkyl" as used alone or as part of another group refers to an alkyl as defined herein, having an aryl substituent. Representative examples of arylalkyl include, but are not limited to, benzyl, 2-phenylethyl, 3-phenylpropyl, benzhydryl, naphthylmethyl, 4-trifluoromethylphenylpropyl and the like.

The term "halogen" or "halo" as used herein alone or as part of another group refers to chlorine, bromine, fluorine and iodine and also to pseudohalogen groups such as trifluoromethyl, trifluoromethoxy and difluoromethoxy.

Unless otherwise indicated, the term "alkoxy" or "aryloxy" as employed herein alone or as part of another group refers to an alkyl or aryl group, as defined herein, linked to an oxygen atom.

Unless otherwise indicated, the term "heteroaryl" as used herein alone or as part of another group refers to a 5- or 6-membered aromatic ring which includes 1, 2, 3 or 4 heteroatoms such as nitrogen, oxygen or sulfur, and includes possible N-oxides. Examples of heteroaryl groups include the following:

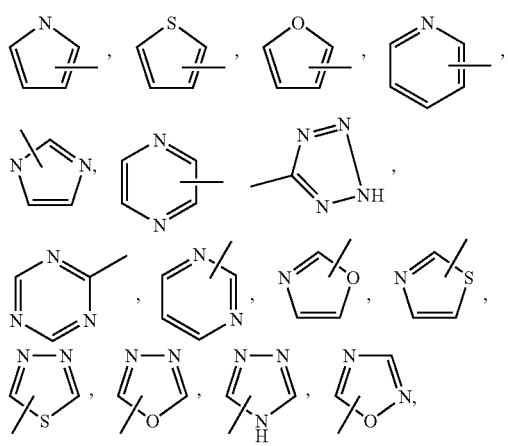

-continued

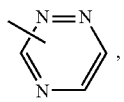

and the like.

Heteroaryl groups as defined above may optionally be substituted with alkyl groups containing up to six carbons and/or with halogen groups.

As used herein, the term "heteroarylalkyl" means an alkyl group having a heteroaryl substituent.

The term "cyano" as used herein, refers to a —CN group.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methyl- or p-toluenesulfonic acid. Corresponding acid addition salts can also be formed having, if desired, an additionally present basic center. The compounds of formula I having at least one acid group (for example COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl, tert-butyl, diethyl, diisopropyl, triethyl, tributyl or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate or nitrate salts.

Preferred salts of the compounds of formula I which contain an acid group include sodium, potassium and magnesium salts and pharmaceutically acceptable organic amine salts.

Any compound that can be converted in vivo to provide the bioactive agent (i.e., the compound of formula I) is a prodrug within the scope and spirit of the invention.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113–191 (Harwood Academic Publishers, 1991); and d) *Hydrolysis in Drug and Prodrug Metabolism*, Bernard Testa and Joachim M. Mayer, (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers and polymorphs of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, diastereomeric, or polymorphic forms or in mixtures thereof. The processes for preparation can utilize racemates, enantiomers, diastereomers or polymorphs as starting materials. When diastereomeric or enantiomeric products are prepared, they can be separated by conventional methods for example, chromatographic or fractional crystallization.

Synthesis

The compounds of formula I of the invention can be prepared as shown below in the following reaction schemes and description thereof, as well as by using relevant published literature procedures that may be used by one skilled in the art. Exemplary reagents and procedures for these reactions appear hereinafter and in the working Examples.

Compounds of formula I may be prepared by coupling carboxylic acids of formula II with amines of formula III using standard methods for amide bond formation, as known to those skilled in the art, for example, by treating equimolar amounts of compounds II and III in N,N-dimethylformamide solution at room temperature with equimolar amounts of 1-hydroxy-7-azabenzotriazole and 1-[3-dimethylamino)propyl]-3-ethylcarbodiimide hydrochloride.

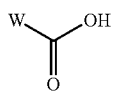

II

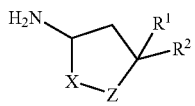

III

Carboxylic acids II may be prepared according to the routes and procedures described in WO 9639384, WO 9926659, and EP 1088824.

Amines III may be prepared by deprotection of the corresponding protected amines IV, in which the amino group is protected (PGN) as a carbamate, amide, phthalimide, N-benzyl derivative, or other standard amine protecting group, such as described in Protective Groups in Organic Synthesis (2$^{nd}$ Edition, T. W. Greene and P. G. M. Wuts, John Wiley & Sons, 1991).

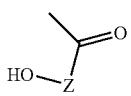

IV

Also included in the definition of protected amine TV are compounds in which the amino group is masked (PGN), i.e., the latent amino group may not fall into the strict definition of a protecting group, such as an azido or nitro group. Protected amines IV wherein the amino group is masked as a carbamate, amide, phthalimide, N-benzyl derivative, or other standard amine protecting group may be prepared from the amines III as described in Protective Groups in Organic Synthesis. A reason for converting an amine III to a protected amine IV would be to modify R$^1$, R$^2$, R$^5$ and/or R$^6$ prior to deprotection to regenerate a different amine III. Azido, nitro, and some protected amino groups, such as benzylamino, may be introduced by other means, such as displacement (azido and benzylamino). Carbamates may be prepared not only from the corresponding amine, but also from carboxylic acids by Curtius rearrangement, via the acid chloride, acyl azide and isocyanate (see Comprehensive Organic Synthesis, Editor B. M. Trost, Pergamon Press, 1991).

Synthetic schemes 1 to 8 provide general synthetic routes for the syntheses of amines III and protected amines IV. The reaction steps are subject to the constraints noted. For example, a reaction step noted "for products wherein R$^2$ is OH" is subject to the constraint that only products in which R$^2$ is OH may be prepared.

Schemes 1, 2 and 8 show different last steps useful for the preparation of amines III. Schemes 3 and 8 show different last steps useful for the preparation of protected amines IV. Schemes 4, 5, 6 and 7 show reaction steps useful for the preparation of intermediates leading to amines III and protected amines IV. Scheme 8 shows amine and protected amine intermediates that may be particularly usefully interconverted using standard amine protecting group chemistry as described in Protective Groups in Organic Synthesis.

SCHEME 1

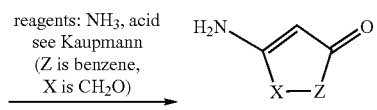

for products wherein
X is CH$_2$O
reagents: a. NaH, BrCH$_2$CO$_2$R
b. NaH
see Kaupmann (Z is benzene)

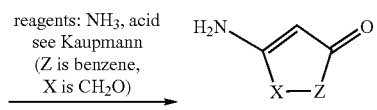

reagents: NH$_3$, acid
see Kaupmann
(Z is benzene,
X is CH$_2$O)

reagents: NaBH$_3$CN, AcOH
see Kaupmann
(Z is benzene, X is CH$_2$O)

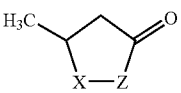

see also Scheme 8 for products wherein
R$^1$ is H and R$^2$ is OH
reagents: NaBH$_4$ or Lib(s-Bu)$_3$H
see Kaupmann (Z is benezene, X is CH$_2$O)

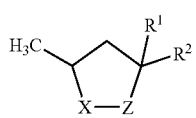

III

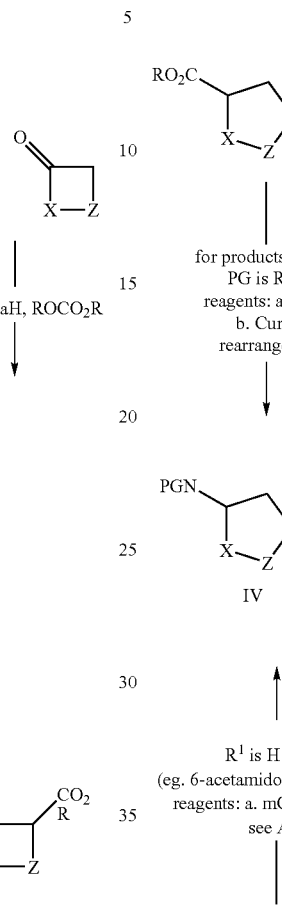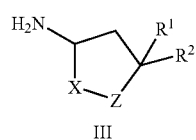

SCHEME 4
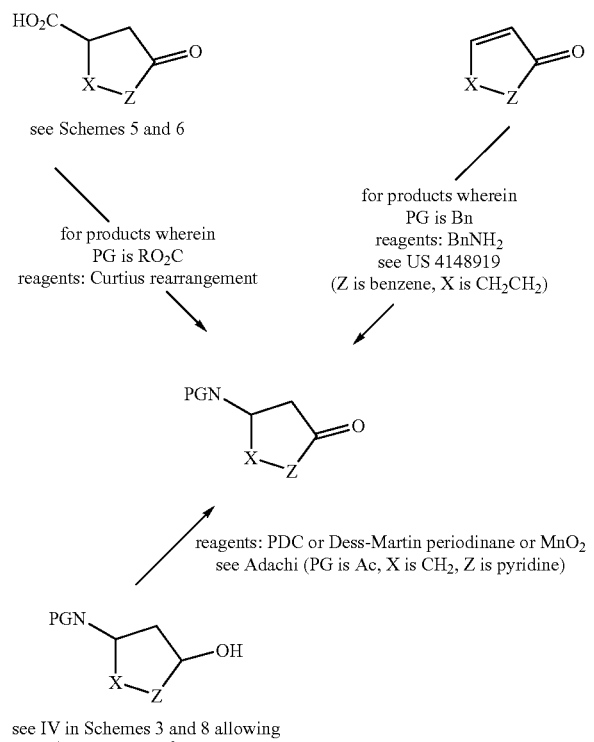
SCHEME 5
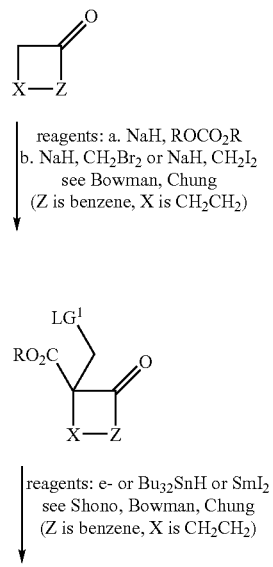
SCHEME 6
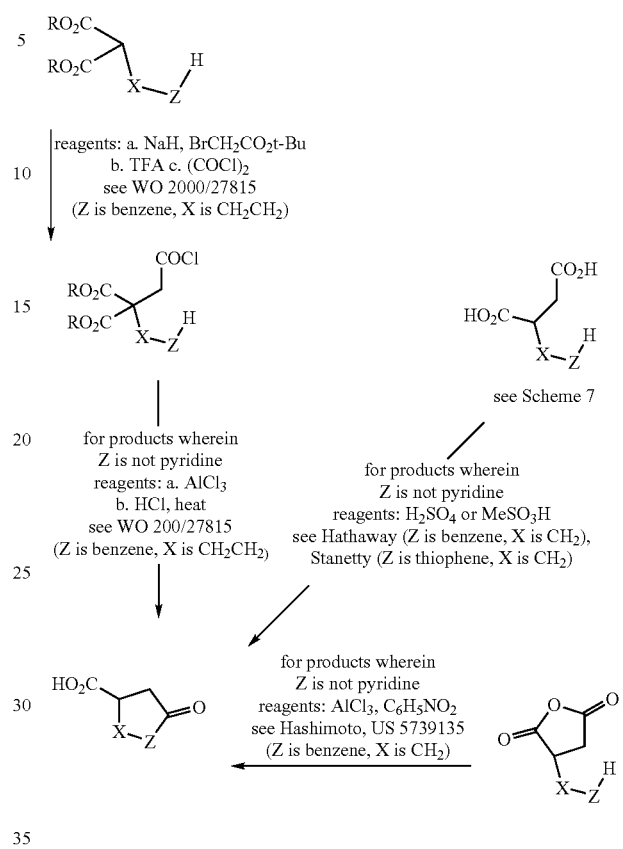
SCHEME 7
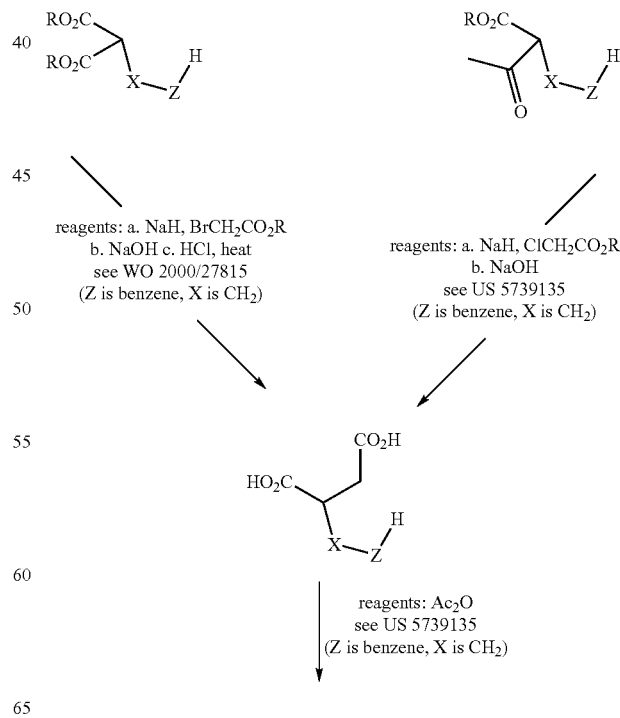

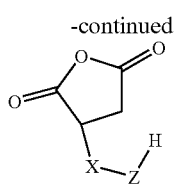

SCHEME 8

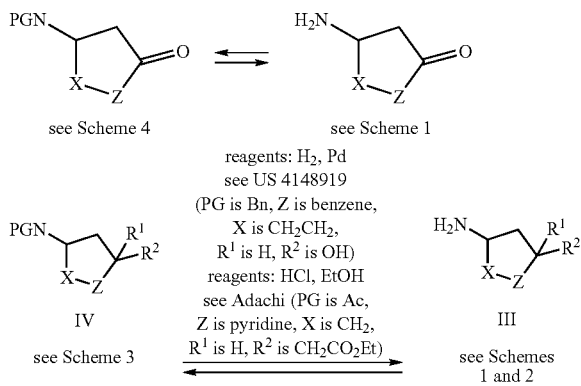

In the synthetic schemes set forth above, the reagent lists are abbreviated. References cited provide full details and in some cases alternative reagents. It is understood that the reagents shown in the synthetic schemes are example reagents, not meant to be limiting. Those skilled in the art will recognize that there are many acids (hydrochloric acid, polyphosphoric acid, etc.), many bases (sodium hydride, potassium methoxide, etc.), many oxidants (hydrogen peroxide, 3-chloroperoxybenzoic acid, Dess-Martin periodinane, etc.), many hydrogenation catalysts (palladium, platinum oxide, Raney® Nickel, etc.), and so on that may be employed to synthesize the compounds of the invention. In some cases alternative reagents known to those skilled in the art will be superior to those listed in the synthetic schemes. Alternative reagents may be found in Reagents For Organic Synthesis (Fieser and Fieser, John Wiley & Sons) and Compendium of Organic Synthetic Methods (John Wiley & Sons). These references will also provide guidance in cases where the synthetic schemes designate only a class of reagent rather than a specific reagent (for example oxidant rather than hydrogen peroxide). In some instances the synthetic schemes refer not to specific reagents or reagent classes, but rather to name reactions, for example Birch reduction (sodium, liquid ammonia; used for reduction of benzene rings to 1,4-cyclohexadienes) and Curtius rearrangement (diphenylphosphoryl azide, alkanol, heat or a. thionyl chloride b. sodium azide c. alkanol, heat; used for conversion of carboxyl groups to alkoxycarbonylamino groups). These name reactions and their experimental details are well-known to those skilled in the art (see Organic Syntheses Based on Name Reactions and Unnamed Reactions, A. Hassner and C. Stumer, Pergamon Press, 1994).

The references provided within the synthetic schemes are not intended to constrain the applicability of the reaction steps, but rather to exemplify the reactions and provide further experimental detail. The references are designated by either a patent/publication number or the first author of a scientific journal publication. Full scientific journal publication references according to first author are as follows:
Adachi, Chem. Pharm. Bull. 1976, 24, 2876–2880;
Bowman, Tet. 1992, 48, 4027–4038;
Chung, Synlett 2001, 1266–1268;
Hasegawa, Tet. Lett. 1998, 39, 4059–4062;
Hashimoto, Org. Prep. & Proc. Int. 1987, 19, 447–449;
Hathaway, J. Med. Chem. 1982, 25, 535–538;
Kaupmann, Eur. J. Med. Chem. 1985, 20, 207–212;
Shiotani, Chem. Pharm. Bull. 1967, 15, 761–767;
Shono, J. Org. Chem. 1990, 55, 5037–5041;
Stanetty, J. Het. Chem. 1996, 33, 1759–1763.

Since those skilled in the art recognize that the efficiency of a planned chemical reaction is often related to the degree of structural similarity between the substrates in the planned reaction and those in a literature procedure being followed, in the synthetic schemes the structural contexts of the relevant transformations described in the references are provided parenthetically.

In the synthetic schemes $LG^1$ and $LG^2$ represent leaving groups, especially chloride, bromide, iodide, methanesulfonate and trifluoromethanesulfonate, which are useful in nucleophilic displacement and palladium catalyzed coupling reactions. The group M as utilized in the above schemes represents a monovalent metal atom or group that renders nucleophilic the group to which it is attached. For example M may be lithium as in butyl lithium, chloromagnesium as in benzylmagnesium chloride, etc. The group R as utilized in the above schemes, (lacking a superscripted numeral) represents an alkyl or benzyl group.

In the synthetic schemes the substituents $R^1$ and $R^2$ are meant to have interchangeable meanings and to differ only as required by their relationship to one another. For example, if a particular reaction scheme shows the synthesis of intermediate IV wherein $R^1$ is hydrogen and $R^2$ is a hydroxyl group, then it is equivalent to say that $R^1$ is the hydroxyl group and $R^2$ is hydrogen, but exactly one of the two must be hydrogen and the other must be a hydroxyl group. The choice of designating a substituent as $R^1$ or $R^2$ in the reaction schemes is generally arbitrary and is not meant to convey stereochemical information.

In general, the interchange of functional groups within $R^1$, $R^2$, $R^5$ and $R^6$, including the formation of various hydrogen bonding groups, may be accomplished according to the methods and procedures described in Compendium of Organic Synthetic Methods (John Wiley & Sons), Comprehensive Organic Functional Group Transformations (Editors A. R. Katritzky, O. Meth-Cohn and C. W. Rees, Pergamon Press) and Comprehensive Organic Transformations—A Guide To Functional Group Preparations (R. C. Larock, VCH Publishers, 1989). For example, a protected amine IV in which $R^1$ is 2-hydroxyethylaminocarbonyl may be prepared from the corresponding compound in which $R^1$ is a carboxyl group by standard amide coupling chemistry using 2-hydroxyethylamine. As another example, a protected amine IV in which $R^1$ is an acylated amino group such as carboxycarbonylamino may be prepared from the corresponding compound in which $R^1$ is a carboxyl group by Curtius rearrangement followed by acylation with methyl oxalyl chloride and ester hydrolysis with sodium hydroxide. It is understood that during the course of manipulating any functional group within $R^1$, $R^2$, R and $R^6$, standard protecting groups, as described in Protective Groups in Organic Synthesis, may be employed to avoid undesired reaction of any other functional group, or of the indole ring or other bicyclic heterocycle W, particularly at its nitrogen, or of the amide linking W to the rest of the molecule.

Standard protecting groups may be used at any stage of the synthesis, for example in manipulating a functional group to convert one compound of formula I to another compound of formula I, or in manipulating a functional group to convert one protected amine IV to another protected amine IV, or to avoid undesired reaction during the coupling of carboxylic acid II and amine III, or during the sequence of steps leading to the formation of either carboxylic acid II or protected amine IV.

Protected amines IV in which $R^1$ or $R^2$ is a hydroxyl group of desired stereochemistry, for instance cis to the PGN group, may be prepared from the corresponding protected amines IV in which the hydroxyl group has undesired stereochemistry, for instance trans to the PGN group, by Mitsunobu inversion as known to those skilled in the art.

Protected amines IV in which $R^1$ or $R^2$ is hydrogen may be prepared from the corresponding protected amines IV in which $R^1$ or $R^2$ is a hydroxyl group by Barton radical deoxygenation or catalytic hydrogenation as known to those skilled in the art.

The ketone intermediate denoted # (a subset of protected amine IV with $R^1$ and $R^2$ together being oxo) is a particularly useful intermediate owing to the myriad of methods available for elaboration of ketone carbonyl groups that are known to those skilled in the art. The reader is directed to Compendium of Organic Synthetic Methods, Comprehensive Organic Functional Group Transformations and Comprehensive Organic Transformations—A Guide To Functional Group Preparations to fully appreciate the utility of intermediate # because the number of useful transformations of intermediate # by reaction of its ketone carbonyl group is too large to be listed in the synthetic schemes. For example, an additional way in which to use intermediate # is by Wittig or Horner-Emmons olefination (sodium hydride and triethyl phosphonoacetate) followed by optional catalytic hydrogenation (hydrogen and palladium on carbon) to provide protected amines IV in which $R^1$ and $R^2$ are together carboethoxymethylidene or $R^1$ is hydrogen and $R^2$ is carboethoxymethyl (see Adachi, PG is acetyl, X is $CH_2$, Z is pyridine). Alternatively, intermediate # may be treated with benzyloxyamine to provide the protected amine IV in which $R^1$ and $R^2$ are together benzyloxyimino. Compounds of formula I in which $R^1$ and $R^2$ are together oxo may likewise be transformed into other compounds of formula I by elaboration at the ketone carbonyl group using chemistry known to those skilled in the art.

Protected amines IV in which $R^1$ is a hydroxyl group and $R^2$ is an electron withdrawing group such as carbomethoxy may be prepared from the corresponding protected amines IV in which $R^1$ is hydrogen and $R^2$ is an electron withdrawing group by treatment with a base such as lithium diisopropylamide followed by an oxygenating reagent such as oxygen, 3-chloroperoxybenzoic acid or a 2-sulfonyloxaziridine (Franklin-Davis) reagent.

Compounds of formula I and protected amines IV wherein $R^5$ or $R^6$ is cyano, alkyl, aryl, arylalkyl, heteroarylalkyl, alkoxy, aryloxy or alkenyl may be prepared from compounds of formula I and protected amines IV wherein $R^5$ or $R^6$, respectively, is halo or hydroxy, using various palladium catalyzed coupling procedures as described in Aranyos, et al., J. Am. Chem. Soc. 1999, 121, 4369–4378 and Hamann, et al., J. Am. Chem. Soc. 1998, 120, 7369–7370 and references contained therein, and in recent papers authored by Gregory C. Fu, Stephen L. Buchwald, or John F. Hartwig. These procedures are directly applicable when $R^5$ or $R^6$ is halo. When $R^5$ or $R^6$ is hydroxy, prior activation by conversion of the hydroxyl group to a trifluoromethylsulfonyloxy group, as described in the aforementioned references, is required.

Compounds of formula I and protected amines IV in which $R^1$ or $R^2$ is $OR^{7A}$, $OCO_2R^8$ or $OCONR^{7A}R^{7B}$, or wherein $R^5$ or $R^6$ is substituted or unsubstituted alkoxy or aryloxy, may be prepared by elaboration of the analogous compounds of formula I and protected amines IV wherein $R^1$, $R^2$, $R^5$ or $R^6$, respectively, is hydroxy. For instance, a compound wherein $R^1$ is benzyloxy may be prepared by benzylation of the compound wherein $R^1$ is hydroxy with benzyl bromide. A compound wherein $R^5$ is carbomethoxymethoxy may be prepared from the compound in which $R^5$ is hydroxy by alkylation with methyl bromoacetate. A compound wherein $R^5$ is carboxymethoxy may be prepared by hydrolysis of the compound wherein $R^5$ is carbomethoxymethoxy or carbo-t-butyloxymethoxy. A compound wherein $R^5$ is 2-hydroxyethoxy may be prepared by reduction of the compound wherein $R^5$ is carbomethoxymethoxy or carboxymethoxy. A compound wherein $R^6$ is 2,3-dihydroxypropyloxy may be prepared from the compound wherein $R^6$ is hydroxy by alkylation with glycidyl 3-nitrobenzenesulfonate, followed by epoxide hydrolysis. A compound wherein $R^5$ is aryloxy may be prepared from the compound in which $R^5$ is hydroxy and an aryl halide by various palladium catalyzed coupling procedures as described in Aranyos, et al., J. Am. Chem. Soc. 1999, 121, 4369–4378 and references contained therein, and in recent papers authored by Stephen L. Buchwald.

During the course of synthesis, oxidation of pyridine containing intermediates may at times cause unwanted or premature formation of the pyridine N-oxide. In these instances subsequent reduction of the N-oxide may be accomplished using standard reducing agents as known to those skilled in the art.

The references above are incorporated herein by reference.

Utilities and Combinations

A. Utilities

The compounds of the present invention possess activity as inhibitors of the enzyme glycogen phosphorylase and therefore may be used in the treatment of diseases associated with glycogen phosphorylase activity. Via the inhibition of glycogen phosphorylase, the compounds of the present invention may preferably be employed to inhibit glycogenolysis, thereby interrupting or modulating hepatic glucose production.

Accordingly, the compounds of the present invention can be administered to mammals, preferably humans, for the treatment of a variety of conditions and disorders, including, but not limited to, treating, preventing or slowing the progression of diabetes and related conditions (such as hyperglycemia, impaired glucose tolerance, insulin resistance and hyperinsulinemia), the microvascular complications associated with diabetes (such as retinopathy, neuropathy, nephropathy and delayed wound healing), the macrovascular complications associated with diabetes (cardiovascular diseases such as atherosclerosis, abnormal heart function, myocardial ischemia and stroke), as well as Metabolic Syndrome and its component conditions including hypertension, obesity and dislipidemia (including hypertriglyceridemia, hypercholesterolemia and low HDL), and other maladies such as non-cardiac ischemia, infection and cancer.

Metabolic Syndrome or "Syndrome X" is described in Ford, et al., *J. Am. Med. Assoc.* 2002, 287, 356–359 and Arbeeny, et al., *Curr. Med. Chem.—Imm., Endoc. & Metab. Agents* 2001, 1, 1–24.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may employed in combination with other glycogen phosphorylase inhibitors or one or more other suitable therapeutic agents useful in the treatment of the aforementioned disorders including: anti-diabetic agents; anti-atherosclerotic agents; anti-ischemic agents; anti-infective agents; anti-cancer and cytotoxic agents; anti-hyperglycemic agents; lipid lowering agents; anti-hypertensive agents; anti-obesity agents and appetite suppressants.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones: ciglitazone, pioglitazone, troglitazone, rosiglitazone; PPAR-gamma agonists; PPAR-alpha agonists; PPAR alpha/gamma dual agonists; SGLT2 inhibitors; dipeptidyl peptidase-IV (DPP4) inhibitors; aldose reductase inhibitors; RXR agonists: JTT-501, MCC-555, MX-6054, DRF2593, GI-262570, KRP-297, LG100268; fatty acid oxidation inhibitors: clomoxir, etomoxir; α-glucosidase inhibitors: precose, acarbose, miglitol, emiglitate, voglibose, MDL-25,637, 1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides, as disclosed by Ashworth et al, Bioorg. & Med. Chem. Lett., Vol. 6, No. 22, pp 1163–1166 and 2745–2748 (1996) employing dosages as set out in the above references.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) include GLP-1(1-36) amide, GLP-1(7-36) amide, GLP-1(7-37) (as disclosed in U.S. Pat. No. 5,614,492 to Habener), as well as AC2993 (Amylen) and LY-315902 (Lilly).

Other anti-diabetic agents that can be used in combination with compounds of the invention include ergoset and D-chiroinositol.

Suitable anti-ischemic agents include, but are not limited to, those described in the Physicians' Desk Reference and NHE inhibitors, including those disclosed in WO 99/43663.

Examples of suitable anti-infective agents are antibiotic agents, including, but not limited to, those described in the Physicians' Desk Reference.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors (e.g., CP-529414 (Pfizer)) and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440.

The HMG CoA reductase inhibitors which may be employed in combination with one or more compounds of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, camiglibose, MDL-73,945; beta-agonists: BRL 35135, BRL 37344, Ro 16–8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276–9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023 and galanin receptor agonists.

Other suitable thiazolidinediones include Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", Diabetes, 47, 1841–1847 (1998), and WO 01/21602, the disclosure of which is incorporated herein by reference, employing dosages as set out therein, which compounds designated as preferred are preferred for use herein.

Suitable alpha2 antagonists also include those disclosed in WO 00/59506, employing dosages as set out herein.

Suitable SGLT2 inhibitors include T-1095, phlorizin, WAY-123783 and those described in WO 01/27128.

Suitable DPP4 inhibitors include those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38 (36), 11597-11603, 1999, TSL-225 (tryptophyl-including isoprenoid (*phosphinyl-methyl*)*phosphonates*, as well as other known squalene synthetase *inhibitors*, for *example*, as disclosed in U.S. P*at*. N*os*. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., Ph.D. dissertation, June, 1987, Dept. Med. Chem. U of Utah, Abstract, Table of Contents, pp. 16, 17, 40–43, 48–51, Summary.

The fibric acid derivatives which may be employed in combination with one or more compounds of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future 24, 9–15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd.).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitor for use in combination with the compounds of the invention include SCH48461 (Schering-Plough), as well as those disclosed in Atherosclerosis 115, 45–63 (1995) and J. Med. Chem. 41, 973 (1998).

Examples of suitable ileal $Na^+$/bile acid cotransporter inhibitors for use in combination with the compounds of the invention include compounds as disclosed in Drugs of the Future, 24, 425–430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug and/or an anorectic agent.

Cannabinoid receptor 1 antagonists and inverse agonists which may be optionally employed in combination with compounds of the present invention include rimonabant, SLV 319 and those discussed in D. L. Hertzog, Expert Opin. Ther. Patents 2004, 14, 1435–1452.

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983 and 5,488,064, with AJ9677, L750,355 and CP331648 being preferred.

Examples of lipase inhibitors which may be optionally employed in combination with compounds of the present invention include orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

Examples of thyroid receptor beta compounds which may be optionally employed in combination with compounds of the present invention include thyroid receptor ligands, such as those disclosed in WO97/21993 (U. Cal SF) and WO99/00353 (KaroBio), with compounds of the KaroBio applications being preferred.

The anorectic agent which may be optionally employed in combination with compounds of the present invention include dexamphetamine, phentermine, phenylpropanolamine or mazindol, with dexamphetamine being preferred.

Other compounds that can be used in combination with the compounds of the present invention include CCK receptor agonists (e.g., SR-27897B); galanin receptor antagonists; MCR-4 antagonists (e.g., HP-228); leptin or mimentics; 11-beta-hydroxysteroid dehydrogenase type-1 inhibitors; urocortin mimetics, CRF antagonists, and CRF binding proteins (e.g., RU-486, urocortin).

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5a reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. Additional anti-cancer agents are disclosed in EP 1177791. The compounds of the invention may also be used in conjunction with radiation therapy.

The aforementioned patents and patent applications are incorporated herein by reference.

The above other therapeutic agents, when employed in combination with the compounds of the present invention may be used, for example, in those amounts indicated in the Physician's Desk Reference, as in the patents set out above or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compounds can be administered to a mammalian patient, including humans, monkeys, dogs, etc. by an oral route, for example, in the form of tablets, capsules, beads, granules or powders. Typical solid formulations will contain from about 1 to about 1000 mg of a compound of formula I. The dose for adults is preferably between 1 and 2,000 mg per day, which can be administered in a single dose or in the form of individual doses from 1–4 times per day.

It will be understood that the specific dose level and frequency of dosage for any particular subject can be varied and will depend upon a variety of factors including the potency of the specific compound employed, the metabolic stability and length of action of that compound, the species, age, body weight, general health, sex and diet of the subject, the mode and time of administration, rate of excretion, drug combination, and severity of the particular condition.

Glycogen phosphorylase inhibitor activity of the compounds of the invention may be determined by use of an assay system as set out below.

Assay for Glycogen Phosphorylase Activity

The utility of the compounds of the invention for use in the treatment of diabetes and the other conditions that may be treated with a glycogen phosphorylase inhibitor may be demonstrated in assays for glycogen phosphorylase inhibition in vitro (U.S. Pat. No. 6,107,329), effects on blood sugar and insulin in vivo (U.S. Pat. No. 6,107,329), effects on ischemic tissue damage in vitro (U.S. Pat. No. 6,107,329), and effects on weight and food intake in vivo (WO 00/47206). Compounds deemed herein to possess activity as inhibitors of the enzyme glycogen phosphorylase demonstrate an $IC_{50}$ of 10 μM or lower when measured in the aforementioned glycogen phosphorylase inhibition in vitro assay.

EXAMPLES

The following working Examples serve to better illustrate, but not limit, some of the preferred embodiments of the present invention.

General

Reverse phase preparative HPLC separation employed an octadecyl sulfate (C-18) column eluting with a solvent gradient of solvents A and B, starting with 20% or more of solvent B and finishing with 100% of solvent B. Solvent A was 10% methanol in water, and solvent B was 90% methanol in water. In many cases both solvents A and B contained 0.1% of trifluoroacetic acid, as noted. Reverse phase analytical HPLC employed the same type of column and solvents, except that the solvents contained 0.2% phosphoric acid.

For Examples 1 to 51 see Table 1:

TABLE 1

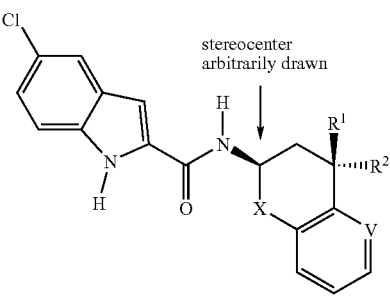

| Example | X | V | $R^1$ | $R^2$ | Stereochem. at center indicated |
|---|---|---|---|---|---|
| 1 | $CH_2$ | CH | OH | $CH_2CN$ | R/S |
| 2 | $CH_2$ | CH | $CH_2CN$ | OH | R/S |
| 3 | $CH_2$ | CH | OH | $CH_2CN$ | homochiral as drawn |
| 4 | $CH_2$ | CH | OH | $CH_2CN$ | homochiral opposite as drawn |
| 5 | $CH_2$ | CH | OH | $CH_2CO_2Et$ | R/S |
| 6 | $CH_2$ | CH | $CH_2CO_2Et$ | OH | R/S |
| 7 | $CH_2$ | CH | OH | $CH_2CO_2H$ | R/S |
| 8 | $CH_2$ | CH | $CH_2CO_2H$ | OH | R/S |
| 9 | $CH_2$ | CH | OH | $CH_2CO_2H$ | homochiral as drawn |
| 10 | $CH_2$ | CH | OH | $CH_2CO_2H$ | homochiral opposite as drawn |
| 11 | $CH_2$ | CH | OH | ![tetrazole with H2C] | R/S |
| 12 | $CH_2$ | CH | OH | $CH_2SO_2Me$ | R/S |
| 13 | $CH_2$ | CH | OH | $CH_2SO_2C_6H_5$ | R/S |
| 14 | $CH_2$ | CH | OH | $CH_2SO_2C_6H_4$-4-OH | R/S |
| 15 | $CH_2$ | CH | OH | $CH_2C_6H_5$ | R/S |
| 16 | $CH_2$ | CH | OH | $CH_2CON(OMe)Me$ | R/S |
| 17 | $CH_2$ | CH | OH | $CH_2CONH_2$ | R/S |
| 18 | $CH_2$ | CH | OH | $CH_2CONHMe$ | R/S |

TABLE 1-continued

| # | | | | | |
|---|---|---|---|---|---|
| 19 | CH$_2$ | CH | OH | 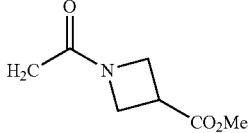 | R/S |
| 20 | CH$_2$ | CH | OH | 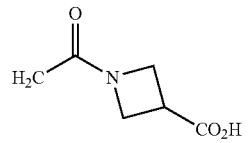 | R/S |
| 21 | CH$_2$ | CH | OH | CH$_2$CON(Me)CH$_2$CN | R/S |
| 22 | CH$_2$ | CH | OH | CH$_2$CONHCH$_2$CO$_2$Me | R/S |
| 23 | CH$_2$ | CH | OH | CH$_2$CONHCH$_2$CO$_2$H | R/S |
| 24 | CH$_2$ | CH | OH | CH$_2$CON(CH$_2$CO$_2$H)$_2$ | R/S |
| 25 | CH$_2$ | CH | OH | 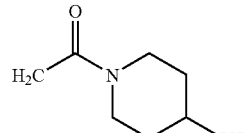 | R/S |
| 26 | CH$_2$ | CH | OH | 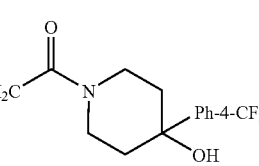 | R/S |
| 27 | CH$_2$ | CH | OH | 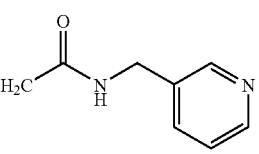 | R/S |
| 28 | CH$_2$ | CH | OH | CH$_2$CONHC$_6$H$_4$-4-OH | R/S |
| 29 | CH$_2$ | CH | OH | 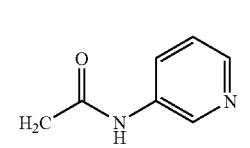 | R/S |
| 30 | CH$_2$ | CH | OH | CH$_2$CONMe$_2$ | homochiral as drawn |
| 31 | CH$_2$ | CH | OH | CH$_2$CON(OMe)Me | homochiral as drawn |
| 32 | CH$_2$ | CH | OH | 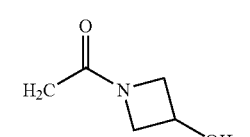 | homochiral as drawn |
| 33 | CH$_2$ | CH | OH | 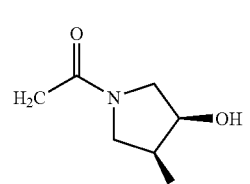 | homochiral as drawn |

TABLE 1-continued

| # | | | | | |
|---|---|---|---|---|---|
| 34 | CH₂ | CH | OH | (1-acetyl-3-hydroxypiperidine structure) | homochiral as drawn |
| 35 | CH₂ | CH | OH | CH₂CONMe₂ | homochiral opposite as drawn |
| 36 | CH₂ | CH | OH | N-acetyl-(S)-leucine structure | homochiral unknown |
| 37 | CH₂ | CH | OH | N-acetyl-(S)-leucine structure | homochiral opposite Example 36 |
| 38 | CH₂ | CH | OH | (2S,4R)-1-acetyl-4-hydroxypyrrolidine-2-carboxylic acid methyl ester | R/S |
| 39 | CH₂ | CH | OH | (2S,4R)-1-acetyl-4-hydroxypyrrolidine-2-carboxylic acid | R/S |
| 40 | CH₂ | CH | OH | N-acetyl-(S)-tyrosine structure | R/S |
| 41 Lithium Salt | CH₂ | CH | OH | (3R,5S)-3,5-dihydroxy-6-acetamidohexanoic acid structure | R/S |
| 42 Lithium Salt | CH₂ | CH | OH | (3R,5S)-3,5-dihydroxy-6-acetamidohexanoic acid structure | homochiral opposite as drawn |
| 43 | CH₂ | CH | CH₂CN | H | R/S |
| 44 | CH₂ | CH | H | CH₂CN | R/S |
| 45 | CH₂ | CH | CH₂CO₂H | H | R/S |
| 46 | CH₂CH₂ | CH | OH | CH₂CN | R/S |
| 47 | CH₂CH₂ | CH | CH₂CN | OH | R/S |
| 48 | CH₂ | CH | together CH₂ | | R/S |
| 49 | CH₂ | N | CH₂SO₂C₆H₅ | OH | R/S |
| 50 | CH₂ | N | OH | CH₂SO₂C₆H₅ | R/S |
| 51 | CH₂ | N | OH | CH₂CO₂Et | R/S |

Example 1

Part I: 2-Benzyl-2-carboxysuccinic acid triethyl ester

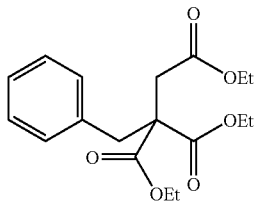

A mixture of diethyl benzylmalonate (100 g, 0.4 mol), ethyl chloroacetate (53.8 g, 0.44 mol) and sodium ethoxide (30 g, 0.44 mol) in absolute ethanol (500 ml) was stirred at 40° C. for 4 h under argon. The solvent was removed under reduced pressure to yield a residue, which was dissolved in ethyl acetate (1 L). The organic layer was washed with water, dried over anhydrous sodium sulfate, and evaporated under vacuum to obtain the title compound as a light yellow oil (130 g, 96% yield), which was used in the next step without further purification. $^1$HNMR (CDCl$_3$) δ 7.02–7.27 (m, 5H), 4.13–4.24 (m, 6H), 3.38 (s, 2H), 2.84 (s, 2H), 1.23–1.30 (m, 9H).

Part II: 2-Benzylsuccinic acid

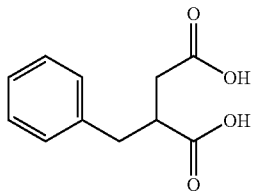

A mixture of 2-benzyl-2-carboxysuccinic acid triethyl ester (130 g, 0.355 mol) and sodium hydroxide (46.85 g, 1.17 mol) in ethanol-water (1:1, 1 L) was stirred at 80° C. for 2 h. After this time, the reaction mixture was cooled to room temperature, and solid that had formed was collected by filtration, washed with cold ethanol, and then added to 6.0 M aqueous hydrochloric acid solution (300 mL). The resulting mixture was stirred at 105° C. for 8 h before cooling to room temperature. Solid was collected by filtration, washed with water, and then dried to obtain the title compound (61.05 g, yield 82.6%). $^1$HNMR (DMSO-d$_6$) 12.6 (bs, 2H), 7.38–7.10 (m, 5H), 3.10–2.84 (m, 1H), 2.80–2.65 (m, 1H), 2.55–2.34 (m, 2H), 2.30–2.12 (m, 1H).

Part III: 3-Carboxy-1-oxo-1,2,3,4-tetrahydronaphthalene

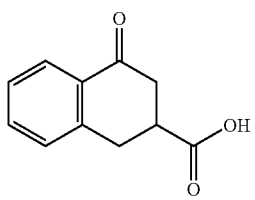

A solution of 2-benzylsuccinic acid (78.37 g, 0.376 mol) in sulfuric acid (98%, 300 mL) was stirred at 60° C. for 20 min, then poured onto ice (2 kg), followed by extraction with diethyl ether (2 L, twice). The organic phase was washed with water, dried over anhydrous sodium sulfate, and evaporated under vacuum to obtain a solid. The solid was recrystallized from ethyl acetate to obtain the title compound (65.14 g, yield 91%). $^1$HNMR (DMSO-d$_6$) δ 12.4–12.2 (bs, 1H), 7.80 (d, J=7.8 Hz, 1H), 7.50 (m, 1H), 7.34–7.28 (m, 2H), 3.21–3.07 (m, 3H), 2.73 (m, 2H). See also U.S. Pat. No. 5,739,135; J. Med. Chem. 1982, 25, 535–538; Org. Prep. Proc. Int. 1987, 19, 447–449.

Part IV: 3-Isocyanato-1-oxo-1,2,3,4-tetrahydronaphthalene

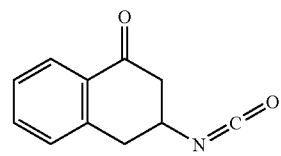

To a mixture of 3-carboxy-1-oxo-1,2,3,4-tetrahydronaphthalene (22 g) and phosphorus oxychloride (5 mL) in diethyl ether (120 mL) was added phosphorus pentachloride (24 g). After an immediate exothermic reaction was observed, the resulting solution was refluxed for 45 min. The mixture was evaporated, then coevaporated with toluene to remove traces of phosphorus oxychloride. The resulting white solid (the acid chloride of the starting acid) was dissolved in 1,4-dioxane (70 mL) and this solution was added dropwise to a stirring solution of sodium azide (13 g) in a mixture of water (50 mL) and 1,4-dioxane (50 mL) maintained a 4–8° C. The resulting mixture was stirred at 4–8° C. for 10 min and then water (250 mL) was added. The resulting white crystalline precipitate was collected by filtration and dissolved in benzene (200 mL). The resulting solution was dried over anhydrous magnesium sulfate and then heated to reflux, which resulted in gas evolution. Reflux was continued until gas evolution ceased. Upon cessation of gas evolution, the solvent was evaporated to yield the title compound (16 g) as a pale yellow liquid.

Part V: 3-Benzyloxycarbonylamino-1-oxo-1,2,3,4-tetrahydronaphthalene

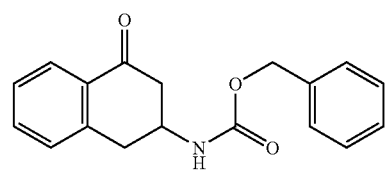

A solution of 3-isocyanato-1-oxo-1,2,3,4-tetrahydronaphthalene (10 g), benzyl alcohol (7.3 g), dry pyridine (3 mL), and benzene (50 mL) was refluxed for 90 min. At the conclusion of this period, the solution was cooled to room temperature, diluted with benzene (150 mL), and then washed with 5% aqueous hydrochloric acid solution (60 mL twice). The organic layer was dried and evaporated under vacuum to yield a residue. The residue was crystallized by dissolving in benzene (35 mL) and diluting with petroleum ether (25 mL). Crystals thus obtained were recrystallized in the same manner to obtain the title compound (6.6 g, mp 79.5–81.5° C.).

The title compound of Part V can also be prepared from the title compound of Part III in the following manner:

To a stirred suspension of 3-carboxy-1-oxo-1,2,3,4-tetrahydronaphthalene (500 mg, 2.63 mmol) in toluene (8 mL) at room temperature under nitrogen was added diphenylphosphoryl azide (0.62 mL, 2.89 mmol) followed by triethylamine (0.4 mL, 2.89 mmol). After 30 min, benzyl alcohol (0.54 mL, 5.26 mmol) was added and the reaction mixture was heated to 60° C. for 5 h. After this time, the reaction mixture was concentrated under vacuum and purified by silica gel chromatography (eluted with 30% ethyl acetate in hexane) to obtain the title compound (495 mg, 64%) as a thick oil. $^{13}$C NMR (400 MHz, CDCl$_3$) δ 195.7, 155.4, 140.5, 136.1, 134.00, 131.9, 129.3, 128.4, 128.1, 128.0, 127.1, 127.0, 66.7, 47.1, 44.7, 35.8. $^1$H NMR (400 MHz, CDCl$_3$) δ 7.99 (d, J=7.5 Hz, 1H), 7.49 (t, J=7.5 Hz, 1H), 7.30 (m, 6H), 7.24 (d, J=7.6 Hz, 1H), 5.34 (d, J=7.0 Hz, 1H), 5.06 (s, 2H), 4.32 (br s, 1H), 3.25 (d, J=15.8 Hz, 1H), 2.98 (m, 1H), 2.89 (dd, J=3.5, 16.7 Hz, 1H), 2.67 (m, 1H).

Part VI: 3-Benzyloxycarbonylamino-1-cyanomethyl-1-hydroxy-1,2,3,4-tetrahydronaphthalene

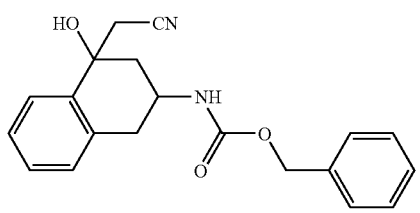

To a stirred solution of n-butyllithium in hexane (42 mL, 1.6 M) under nitrogen at −80° C., was added dry tetrahydrofuran (40 mL). To this was added over a 7 min period a solution of dry acetonitrile (2.8 g, distilled from phosphorus pentoxide) in dry tetrahydrofuran (40 mL). The resulting white suspension was stirred for 1 h at −80° C. After this time, a solution of 3-benzyloxycarbonylamino-1-oxo-1,2,3,4-tetrahydronaphthalene (9.9 g) in dry tetrahydrofuran (40 mL) was added over a 5 min period. Additional tetrahydrofuran (40 mL) was introduced to facilitate stirring. After an additional 10 min at −80° C., the reaction mixture was allowed to slowly warm to room temperature during a 15 min period. Once at room temperature, the reaction mixture was poured into a mixture of ice, concentrated aqueous hydrochloric acid solution (10 mL), and diethyl ether (100 mL). The organic layer was separated, and the aqueous layer was extracted with diethyl ether (50 mL twice). The combined organic layers were washed with water (50 mL twice), dried, and evaporated to yield a residue. The residue was chromatographed on silica gel to obtain the title compound as a mixture of diastereomers (7.5 g).

Part VII: R/S-(1R*,3R*)-3-benzyloxycarbonylamino-1-cyanomethyl-1-hydroxy-1,2,3,4-tetrahydronaphthalene and R/S-(1S*,3R*)-3-benzyloxycarbonylamino-1-cyanomethyl-1-hydroxy-1,2,3,4-tetrahydronaphthalene

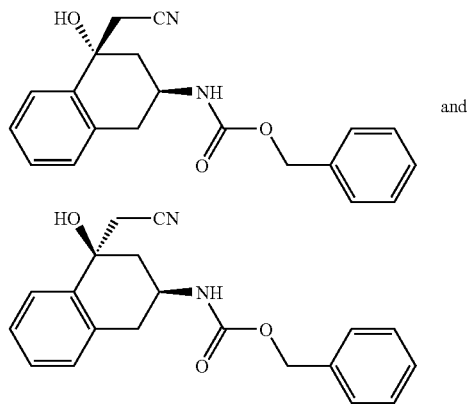

A small sample of 3-benzyloxycarbonylamino-1-cyanomethyl-1-hydroxy-1,2,3,4-tetrahydronaphthalene was purified by silica gel chromatography followed by further purification by reverse phase preparative HPLC (trifluoroacetic acid containing solvents were used) to obtain R/S-(1R*,3R*)-3-benzyloxycarbonylamino-1-cyanomethyl-1-hydroxy-1,2,3,4-tetrahydronaphthalene (eluted first, 10 mg) and R/S-(1S*,3R*)-3-benzyloxycarbonylamino-1-cyanomethyl-1-hydroxy-1,2,3,4-tetrahydronaphthalene (eluted second, 33 mg).

Part VIII: R/S-(1S*,3R*)-3-amino-1-cyanomethyl-1-hydroxy-1,2,3,4-tetrahydronaphthalene

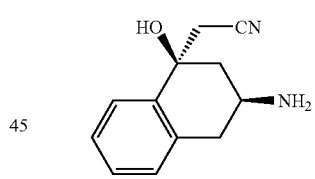

To a solution of R/S-(1S*,3R*)-3-benzyloxycarbonylamino-1-cyanomethyl-1-hydroxy-1,2,3,4-tetrahydronaphthalene (55 mg) in ethanol (3 mL) at room temperature was added 10% palladium on carbon (10 mg). Hydrogen gas was bubbled through the mixture for 15 min, and then the reaction mixture was stirred under a hydrogen balloon for 7 h. After this time, the reaction mixture was filtered through Celite®, and then evaporated under vacuum to obtain the title compound (25 mg) as a white solid.

Part IX: Example 1

To a solution of R/S-(1S*,3R*)-3-amino-1-cyanomethyl-1-hydroxy-1,2,3,4-tetrahydronaphthalene (25 mg) in tetrahydrofuran (1 mL) was added diisopropylethylamine (0.043 mL), 1-(3-dimethylaminopropyl)-3-ethylcarbodiimide hydrochloride (47 mg), 1-hydroxy-7-azabenzotriazole (34 mg) and 5-chloroindole-2-carboxylic acid (27 mg). After stirring for 30 min at room temperature under nitrogen, the reaction mixture was diluted with ethyl acetate, and then washed sequentially with 1.0 M aqueous hydrochloric acid solution, 1.0 M aqueous sodium hydroxide solution, and brine. The organic layer was dried over anhydrous magnesium sulfate and evaporated under vacuum to provide a residue. The residue was purified by reverse phase preparative HPLC (trifluoroacetic acid containing solvents were used) to obtain Example 1 (25 mg). MS [M−H]⁻, 378.

Example 2

Example 2 was prepared from R/S-(1R*,3R*)-3-benzyloxycarbonylamino-1-cyanomethyl-1-hydroxy-1,2,3,4-tetrahydronaphthalene by procedures analogous to those described for the preparation of Example 1 from R/S-(1S*,3R*)-3-benzyloxycarbonylamino-1-cyanomethyl-1-hydroxy-1,2,3,4-tetrahydronaphthalene. MS [M−H]⁻, 378.

Example 3

Example 3 was prepared from (R)-3-carboxy-1-oxo-1,2,3,4-tetrahydronaphthalene (prepared by resolution of racemic 3-carboxy-1-oxo-1,2,3,4-tetrahydronaphthalene with (−)-α-ethylbenzylamine in the manner disclosed in WO 00/27815) by procedures analogous to those described for the preparation of Example 1 from racemic 3-carboxy-1-oxo-1,2,3,4-tetrahydronaphthalene. HPLC/MS [M+H]⁺, 380; [M−H]⁻, 378.

Alternatively, Example 3 was prepared from Example 1 by separation on chiral normal phase preparative HPLC (Chiralcel AD column, 50% isopropanol in hexane was used). Example 3 eluted before Example 4. The structure of Example 3 was confirmed by x-ray crystallography.

Example 4

Example 4 was prepared from (S)-3-carboxy-1-oxo-1,2,3,4-tetrahydronaphthalene (prepared by resolution of racemic 3-carboxy-1-oxo-1,2,3,4-tetrahydronaphthalene with (+)-α-ethylbenzylamine in the manner disclosed in WO 00/27815) by procedures analogous to those described for the preparation of Example 1 from racemic 3-carboxy-1-oxo-1,2,3,4-tetrahydronaphthalene. HPLC/MS [M+H]⁺, 380; [M−H]⁻, 378.

Alternatively, Example 4 was prepared from Example 1 by separation on chiral normal phase preparative HPLC (Chiralcel AD column, 50% isopropanol in hexane was used). Example 3 eluted before Example 4.

Example 5

Part I: R/S-(1R*,3R*)-3-benzyloxycarbonylamino-1-carboethoxymethyl-1-hydroxy-1,2,3,4-tetrahydronaphthalene and R/S-(1S*,3R*)-3-benzyloxycarbonylamino-1-carboethoxymethyl-1-hydroxy-1,2,3,4-tetrahydronaphthalene

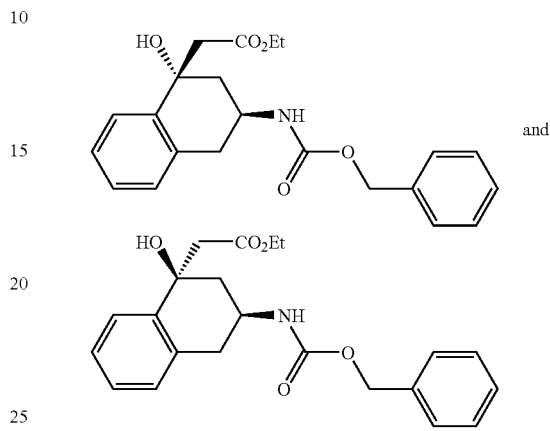

Ethyl acetate (0.66 mL) was added to a stirring solution of lithium hexamethyldisilazide (1.0 M in tetrahydrofuran, 0.68 mL) in tetrahydrofuran (5 mL) at −78° C. under nitrogen. The mixture was stirred for 1 h before it was transferred by cannula to a stirring solution of 3-benzyloxycarbonylamino-1-oxo-1,2,3,4-tetrahydronaphthalene (as prepared in Part V, Example 1, 400 mg) in tetrahydrofuran (5 mL) at −78° C. under nitrogen. After 10 min, the cold bath was removed and the reaction mixture was diluted with water, saturated aqueous ammonium chloride solution and ethyl acetate. The layers were separated and the aqueous layer was extracted with ethyl acetate. The combined organic layers were dried over anhydrous magnesium sulfate and evaporated under vacuum to yield a residue. The residue was purified by reverse phase preparative HPLC (trifluoroacetic acid containing solvents were used) to obtain R/S-(1R*,3R*)-3-benzyloxycarbonylamino-1-carboethoxymethyl-1-hydroxy-1,2,3,4-tetrahydronaphthalene (48 mg) and R/S-(1S*,3R*)-3-benzyloxycarbonylamino-1-carboethoxymethyl-1-hydroxy-1,2,3,4-tetrahydronaphthalene (0.38 g).

Part II: R/S-(1S*,3R*)-3-amino-1-carboethoxymethyl-1-hydroxy-1,2,3,4-tetrahydronaphthalene

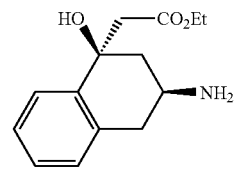

To a solution of R/S-(1S*,3R*)-3-benzyloxycarbonylamino-1-carboethoxymethyl-1-hydroxy-1,2,3,4-tetrahydronaphthalene (0.29 g) in ethanol (5 mL) at room temperature was added 10% palladium on carbon (82 mg). Upon completion of addition, hydrogen gas was bubbled through the mixture for 10 min. After this time, the reaction mixture was stirred under a hydrogen balloon for 8 h. At the conclusion of this period, the reaction mixture was filtered through Celite® and rinsed with ethanol and ethyl acetate. The filtrate was evaporated under vacuum to obtain the title compound (186 mg) as a white solid.

Part III: Example 5

To a solution of R/S-(L S*,3R*)-3-amino-1-carboethoxymethyl-1-hydroxy-1,2,3,4-tetrahydronaphthalene (100 mg) in tetrahydrofuran (5 mL) was added diisopropylethylamine (0.140 mL), 1-(3-dimethylaminopropyl)-3-ethylcarbodiimide hydrochloride (154 mg), 1-hydroxy-7-azabenzotriazole (109 mg) and 5-chloroindole-2-carboxylic acid (86 mg). After stirring for 15 min at room temperature under nitrogen, the reaction mixture was diluted with ethyl acetate, and then washed sequentially with 1.0 M aqueous hydrochloric acid solution, 1.0 M aqueous sodium hydroxide solution, and brine. The organic layer was dried over anhydrous magnesium sulfate and evaporated under vacuum to yield crude product. Methanol was added to this crude product and the resulting yellow solid was collected by filtration to obtain Example 5 (120 mg). MS [M–H]$^-$, 425.

Example 6

Example 6 was prepared from R/S-(1R*,3R*)-3-benzyloxycarbonylamino-1-carboethoxymethyl-1-hydroxy-1,2,3,4-tetrahydronaphthalene by procedures analogous to those used in the preparation of Example 5 from R/S-(1S*,3R*)-3-benzyloxycarbonylamino-1-carboethoxymethyl-1-hydroxy-1,2,3,4-tetrahydronaphthalene. MS [M–H]$^-$, 425.

Example 7

Example 5 (245 mg) and lithium hydroxide monohydrate (69 mg) were dissolved in a mixture of tetrahydrofuran and water (1:1, 2 μL). The resulting mixture was stirred at room temperature under nitrogen for 2 h. The tetrahydrofuran was then removed under reduced pressure, and the remaining aqueous mixture was acidified to pH 1 with 1.0 M aqueous hydrochloric acid solution. The resulting white solid was collected by filtration to obtain Example 7 (209 mg). MS [M–H]$^-$, 397.

Example 8

Example 8 was prepared from Example 6 following procedures analogous to those used in the preparation of Example 7 from Example 5. MS [M–H]$^-$, 397.

Example 9

Example 9 was prepared from (R)-3-carboxy-1-oxo-1,2,3,4-tetrahydronaphthalene following procedures analogous to those used to prepare Example 7 from 3-carboxy-1-oxo-1,2,3,4-tetrahydronaphthalene. MS [M–H]$^-$, 397. The structure of Example 9 was confirmed by x-ray crystallography.

Example 10

Example 10 was prepared from (S)-3-carboxy-1-oxo-1,2,3,4-tetrahydronaphthalene following procedures analogous to those used to prepare Example 7 from 3-carboxy-1-oxo-1,2,3,4-tetrahydronaphthalene. MS [M–H]$^-$, 397.

Example 11

Part I: R/S-(1R*,3R*)-3-benzyloxycarbonylamino-1-hydroxy-1-(2-trityl-2H-tetrazol-5-ylmethyl)-1,2,3,4-tetrahydronaphthalene and R/S-(1S*,3R*)-3-benzyloxycarbonylamino-1-hydroxy-1-(2-trityl-2H-tetrazol-5-ylmethyl)-1,2,3,4-tetrahydronaphthalene

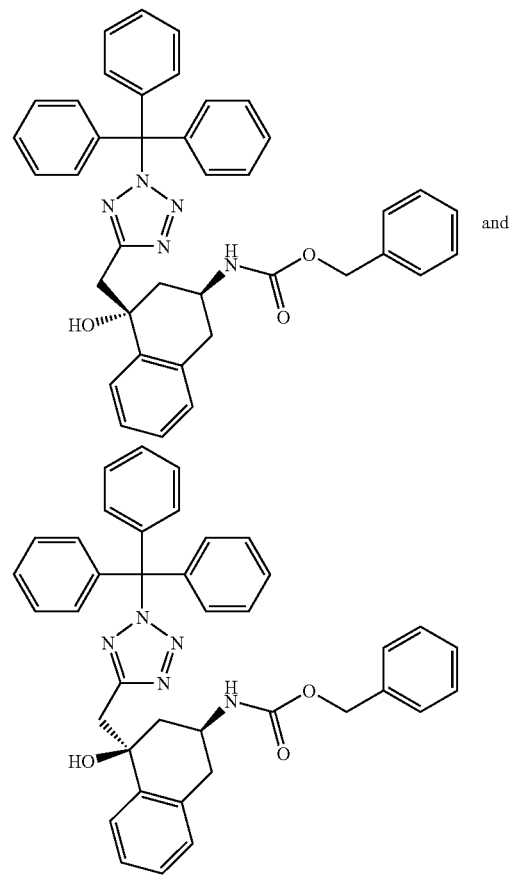

To a stirring solution of 2-trityl-5-methyl tetrazole (prepared in the manner disclosed in Tetrahedron Lett. 1996, 37, 3655–3658; 0.16 g) in tetrahydrofuran (3.4 mL) under nitrogen at −78° C. was added n-butyllithium (1.92 M solution in hexane, 0.28 mL) dropwise. The resulting deep red solution was stirred at the same temperature for 1 h before a solution of 3-benzyloxycarbonylamino-1-oxo-1,2,3,4-tetrahydronaphthalene (200 mg) in tetrahydrofuran (1 mL) was added. After 30 min, the cold bath was removed and the yellow reaction mixture was warmed to room temperature. After 30 min at room temperature, the reaction mixture was diluted with ethyl acetate and saturated aqueous ammonium chloride solution. The organic layer was washed with brine, dried over anhydrous magnesium sulfate and evaporated under vacuum to yield a residue. The residue was purified by reverse phase preparative HPLC (trifluoroacetic acid containing solvents were used) to obtain R/S—(1R*,3R*)-3-benzyloxycarbonylamino-1-hydroxy-1-(2-trityl-2H-tetrazol-5-ylmethyl)-1,2,3,4-tetrahydronaphthalene (17.4 mg), R/S-(1S*,3R*)-3-benzyloxycarbonylamino-1-hydroxy-1-(2-trityl-2H-tetrazol-5-ylmethyl)-1,2,3,4-tetrahydronaphthalene (30 mg) and recovered ketone starting material (84 mg).

Part II: R/S-(1S*,3R*)-3-benzyloxycarbonylamino-1-hydroxy-1-(2H-tetrazol-5-ylmethyl)-1,2,3,4-tetrahydronaphthalene

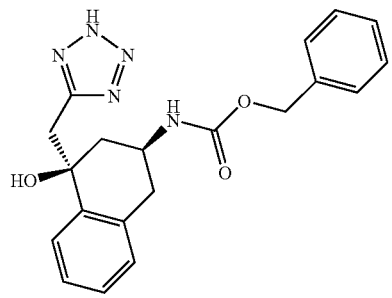

To a solution of R/S-(1S*,3R*)-3-benzyloxycarbonylamino-1-hydroxy-1-(2-trityl-2H-tetrazol-5-ylmethyl)-1,2,3,4-tetrahydronaphthalene (100 mg) in methanol and tetrahydrofuran (1:1, 16 mL) under nitrogen was added concentrated aqueous hydrochloric acid solution (2 mL). After stirring at room temperature for 16 h, the reaction mixture was evaporated under vacuum and purified by reverse phase preparative HPLC (trifluoroacetic acid containing solvents were used) to obtain the title product (33 mg).

Part III: R/S-(1S*,3R*)-3-amino-1-hydroxy-1-(2H-tetrazol-5-ylmethyl)-1,2,3,4-tetrahydronaphthalene

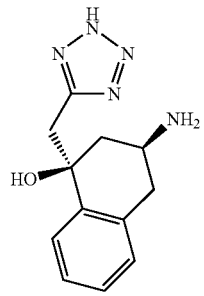

R/S-(1S*,3R*)-3-benzyloxycarbonylamino-1-hydroxy-1-(2H-tetrazol-5-ylmethyl)-1,2,3,4-tetrahydronaphthalene (33 mg) was dissolved in ethanol (1 mL) with stirring at room temperature. The resulting solution was hydrogenated (balloon) for 16 h in the presence of 10% palladium on carbon. The reaction mixture was filtered through Celite®, and then evaporated under vacuum to obtain the title compound (29 mg).

Part IV: Example 11

R/S-(1S*,3R*)-3-amino-1-hydroxy-1-(2H-tetrazol-5-ylmethyl)-1,2,3,4-tetrahydronaphthalene (29 mg) and 5-chloroindole-2-carboxylic acid (25 mg) were coupled by a procedure analogous to the procedure described in Part III, Example 5 to yield crude product. The crude product was purified by reverse phase preparative HPLC (trifluoroacetic acid containing solvents were used) to obtain Example 11 (2 mg). MS [M−H]−, 421.

Example 12

Part I: 3-Benzyloxycarbonylamino-1-hydroxy-1-methanesulfonylmethyl-1,2,3,4-tetrahydronaphthalene

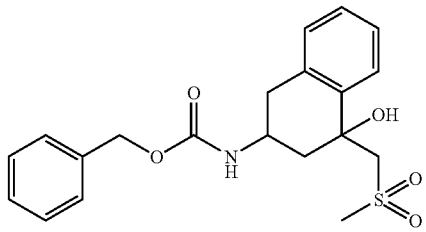

To a solution of methyl sulfone (64 mg) in tetrahydrofuran (4 mL) stirring at −78° C. under nitrogen was slowly added lithium hexamethyldisilazide (1.0 M tetrahydrofuran solution, 0.67 mL). The resulting mixture was stirred for 1 h to form lithio methyl sulfone, and then a solution of 3-benzyloxycarbonylamino-1-oxo-1,2,3,4-tetrahydronaphthalene (40 mg) in tetrahydrofuran (0.4 mL) was added. Upon completion of addition, the resulting mixture was stirred for 30 min at −78° C. After this time, the reaction mixture was allowed to warm to room temperature at which it was stirred for 16 h. At the conclusion of this period, the reaction mixture was analyzed by HPLC, which indicated that starting material was still present. The reaction mixture was again cooled to −78° C. and additional lithio methyl sulfone mixture (prepared from methyl sulfone, 64 mg, in the manner set forth above) was added. The resulting mixture was stirred for 30 minutes and then analyzed by HPLC, which indicated that the starting material had been consumed. The reaction mixture was quenched at −78° C. with saturated aqueous ammonium chloride solution, warmed to room temperature, and extracted with ethyl acetate. The organic layer was washed with brine, dried over anhydrous magnesium sulfate, and evaporated under vacuum to yield a residue. The residue was purified by reverse phase preparative HPLC (trifluoroacetic acid containing solvents were used) to obtain the title compound (23 mg) as a racemic diastereomeric mixture, predominantly the diastereomer leading to Example 12 that results from nucleophilic addition of lithio methyl sulfone to the carbonyl of 3-benzyloxycarbonylamino-1-oxo-1,2,3,4-tetrahydronaphthalene anti to the benzyloxycarbonylamino group.

Part II: 3-Amino-1-hydroxy-1-methanesulfonylmethyl-1,2,3,4-tetrahydronaphthalene, trifluoroacetic acid salt

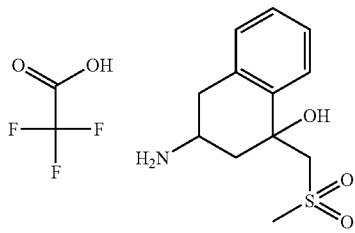

A solution of a 3-benzyloxycarbonylamino-1-hydroxy-1-methanesulfonylmethyl-1,2,3,4-tetrahydronaphthalene (23 mg) in ethanol (0.6 mL) stirring at room temperature was hydrogenated (balloon) in the presence of 10% palladium on carbon (6.3 mg) for 16 h. The reaction mixture was filtered through Celite®, evaporated under vacuum and purified by reverse phase preparative HPLC (trifluoroacetic acid containing solvents were used) to obtain the title compound (10 mg) as a diastereomeric mixture.

Part III: Example 12

3-Amino-1-hydroxy-1-methanesulfonylmethyl-1,2,3,4-tetrahydronaphthalene trifluoroacetic acid salt (10 mg) and 5-chloroindole-2-carboxylic acid (8.4 mg) were coupled by a procedure analogous to the procedure described in Part III, Example 5 to yield crude product. The crude product was purified by reverse phase preparative HPLC (trifluoroacetic acid containing solvents were used) to obtain Example 12 as a 9:1 mixture with its diastereomer according to $^1$H NMR (1.3 mg). MS [M−H]$^−$, 431. The major isomer eluted before the minor isomer when analyzed by reverse phase analytical HPLC.

Example 13

Part I: R/S-(1S*,3R*)-3-benzyloxycarbonylamino-1-hydroxy-1-phenylsulfonylmethyl-1,2,3,4-tetrahydronaphthalene and R/S-(1R*,3R*)-3-benzyloxycarbonylamino-1-hydroxy-1-phenylsulfonylmethyl-1,2,3,4-tetrahydronaphthalene

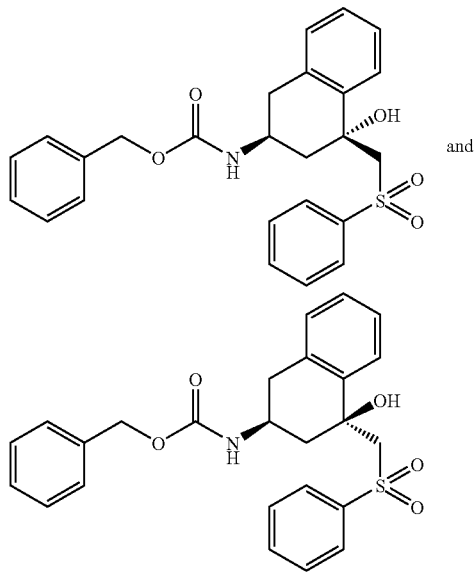

and

To a solution of methyl phenyl sulfone (265 mg) in tetrahydrofuran (10 mL) stirring at −78° C. under nitrogen was slowly added lithium hexamethyldisilazide (1.0 M tetrahydrofuran solution, 1.7 mL). After 1 h, a solution of 3-benzyloxycarbonylamino-1-oxo-1,2,3,4-tetrahydronaphthalene (100 mg) in tetrahydrofuran (1 mL) was added. The reaction mixture was stirred for 30 min at −78° C., quenched with saturated aqueous ammonium chloride solution and then extracted with an ethyl acetate/hexane mixture. The organic layer was washed with brine, dried over anhydrous magnesium sulfate, and evaporated under vacuum to yield a residue. The residue was purified by reverse phase preparative HPLC (trifluoroacetic acid containing solvents were used) to obtain R/S-(1S*,3R*)-3-benzyloxycarbonylamino-1-hydroxy-1-phenylsulfonylmethyl-1,2,3,4-tetrahydronaphthalene (8 mg) and R/S-(1R*,3R*)-3-benzyloxycarbonylamino-1-hydroxy-1-phenylsulfonylmethyl-1,2,3,4-tetrahydronaphthalene (95 mg).

Part II: R/S-(1R*,3R*)-3-amino-1-hydroxy-1-phenylsulfonylmethyl-1,2,3,4-tetrahydronaphthalene, trifluoroacetic acid salt

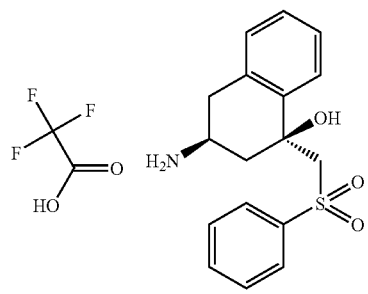

A solution of R/S-(1R*,3R*)-3-benzyloxycarbonylamino-1-hydroxy-1-phenylsulfonylmethyl-1,2,3,4-tetrahydronaphthalene (95 mg) in ethanol (3 mL) stirring at room temperature was hydrogenated (balloon) in the presence of 10% palladium on carbon (9.5 mg) for 2 days. The reaction mixture was filtered through Celite®, evaporated under vacuum and purified by reverse phase preparative HPLC (trifluoroacetic acid containing solvents were used) to obtain the title compound (44 mg) and starting material (8.7 mg).

Part III: Example 13

R/S-(1R*,3R*)-3-amino-1-hydroxy-1-phenylsulfonylmethyl-1,2,3,4-tetrahydronaphthalene, trifluoroacetic acid salt (44 mg) and 5-chloroindole-2-carboxylic acid (22 mg) were coupled by the coupling procedure described in Part III, Example 5 to yield crude product. The crude product was purified by reverse phase preparative HPLC (trifluoroacetic acid containing solvents were used) to obtain Example 13 (13.5 mg) as a white solid. MS [M+H]$^+$, 495.

Example 14

Part I: R/S-(1S*,3R*)-3-benzyloxycarbonylamino-1-hydroxy-1-(4-hydroxyphenylsulfonylmethyl)-1,2,3,4-tetrahydronaphthalene and R/S-(1R*,3R*)-3-benzyloxycarbonylamino-1-hydroxy-1-(4-hydroxyphenylsulfonylmethyl)-1,2,3,4-tetrahydronaphthalene

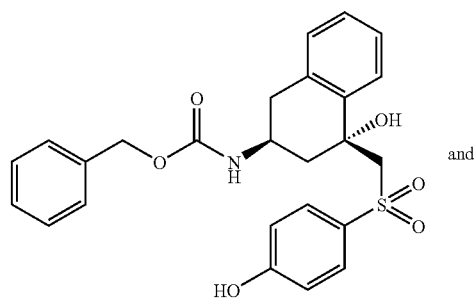

and

-continued

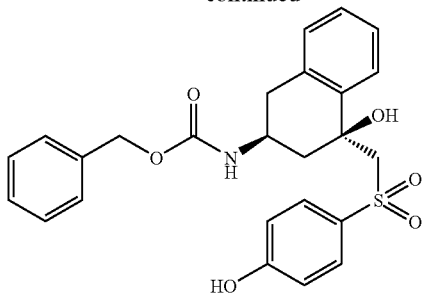

To a solution of lithium hexamethyldisilazide in tetrahydrofuran (1.7 mL of 1.0 M reagent in tetrahydrofuran solution was diluted with 1.0 mL tetrahydrofuran) stirring at −78° C. under nitrogen was added a solution of 4-(methylsulfonyl)phenol (146 mg) in tetrahydrofuran (1 mL). After stirring for 45 min, a solution of racemic 3-benzyloxycarbonylamino-1-oxo-1,2,3,4-tetrahydronaphthalene (50 mg) in tetrahydrofuran (1 mL) was added. Upon completion of addition, the reaction mixture was stirred for 30 min at −78° C. The reaction mixture was then quenched with saturated aqueous ammonium chloride solution, warmed to room temperature, and extracted with ethyl acetate. The organic layer was washed with brine, dried over anhydrous magnesium sulfate, and evaporated under vacuum to yield a residue. The residue was purified by reverse phase preparative HPLC (trifluoroacetic acid containing solvents were used) to obtain R/S-(1S*,3R*)-3-benzyloxycarbonylamino-1-hydroxy-1-(4-hydroxyphenylsulfonylmethyl)-1,2,3,4-tetrahydronaphthalene (19.5 mg) and R/S-(1R*,3R*)-3-benzyloxycarbonylamino-1-hydroxy-1-(4-hydroxyphenylsulfonylmethyl)-1,2,3,4-tetrahydronaphthalene (37 mg).

Part II: R/S-(1R*,3R*)-3-amino-1-hydroxy-1-(4-hydroxyphenylsulfonylmethyl)-1,2,3,4-tetrahydronaphthalene, trifluoroacetic acid salt

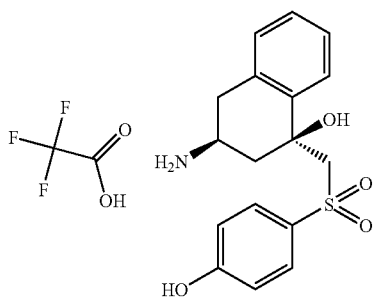

A solution of R/S-(1R*,3R*)-3-benzyloxycarbonylamino-1-hydroxy-1-(4-hydroxyphenylsulfonylmethyl)-1,2,3,4-tetrahydronaphthalene (37 mg) in ethanol (2 mL) stirring at room temperature was hydrogenated (balloon) in the presence of 10% palladium on carbon for 14 h. The reaction mixture was filtered through Celite®, evaporated under vacuum and purified by reverse phase preparative HPLC (trifluoroacetic acid containing solvents were used) to obtain the title compound (13 mg).

Part III: Example 14

R/S-(1R*,3R*)-3-amino-1-hydroxy-1-(4-hydroxyphenylsulfonylmethyl)-1,2,3,4-tetrahydronaphthalene, trifluoroacetic acid salt (13 mg) and 5-chloroindole-2-carboxylic acid (8.6 mg) were coupled by a procedure analogous to the procedure described in Part III, Example 5 to yield crude product. The crude product was purified by reverse phase preparative HPLC (trifluoroacetic acid containing solvents were used) to obtain Example 14 (8 mg) as a white solid. MS [M−H]⁻, 509. NOE studies proved the relative stereochemistry of this product.

Example 15

Part I: R/S-(1R*,3R*)-3-benzyloxycarbonylamino-1-benzyl-1-hydroxy-1,2,3,4-tetrahydronaphthalene

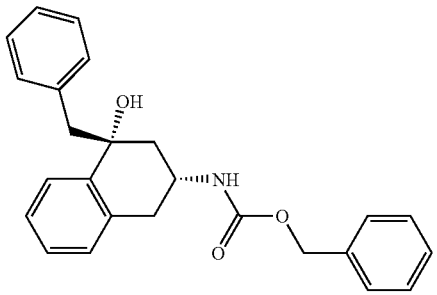

To a solution of racemic 3-benzyloxycarbonylamino-1-oxo-1,2,3,4-tetrahydronaphthalene (50 mg) in tetrahydrofuran (0.5 mL) stirring at room temperature under nitrogen was added benzylmagnesium chloride (2.0 M tetrahydrofuran solution, 0.21 mL). After 6 h, the reaction mixture was quenched with saturated aqueous ammonium chloride solution and extracted with ethyl acetate. The organic layer was washed with brine, dried over anhydrous magnesium sulfate, and evaporated under vacuum to yield a residue. The residue was purified by reverse phase preparative HPLC (trifluoroacetic acid containing solvents were used) to obtain the title compound (18.5 mg).

Part II: R/S-(1R*,3R*)-3-amino-1-benzyl-1-hydroxy-1,2,3,4-tetrahydronaphthalene

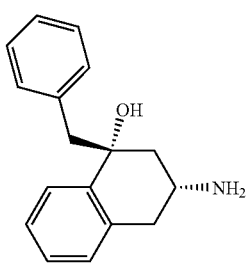

R/S-(1R*,3R*)-3-benzyloxycarbonylamino-1-benzyl-1-hydroxy-1,2,3,4-tetrahydronaphthalene (18.5 mg) was dissolved in ethanol (0.5 mL) stirring at room temperature. The resulting solution was hydrogenated (balloon) in the presence of 10% palladium on carbon (5.1 mg) for 16 h. After this time, the reaction mixture was filtered through Celite® and evaporated under vacuum to obtain the title compound (17.5 mg).

Part III: Example 15

R/S-(1R*,3R*)-3-amino-1-benzyl-1-hydroxy-1,2,3,4-tetrahydronaphthalene (17.5 mg) and 5-chloroindole-2-carboxylic acid (10.4 mg) were coupled by a procedure analogous to the procedure described in Part III, Example 5 to yield crude product. The crude product was purified by reverse phase preparative HPLC (trifluoroacetic acid containing solvents were used) to obtain Example 15 (11.7 mg). MS $[M-H]^-$, 429.

Example 16

To a solution of Example 7 (12 mg) in tetrahydrofuran (1 mL) was added diisopropylethylamine (0.021 mL), 1-(3-dimethylaminopropyl)-3-ethylcarbodiimide hydrochloride (11.5 mg), 1-hydroxy-7-azabenzotriazole (8 mg), and N,O-dimethylhydroxylamine hydrochloride (6 mg). After stirring for 30 min at room temperature under nitrogen, the reaction mixture was diluted with ethyl acetate, then washed sequentially with 1.0 M aqueous hydrochloric acid solution, 1.0 M aqueous sodium hydroxide solution, and brine. The organic layer was dried over anhydrous magnesium sulfate and evaporated under vacuum to yield a crude product. This crude product was purified by reverse phase preparative HPLC (trifluoroacetic acid containing solvents were used) to obtain Example 16 (7 mg) as a white solid. MS $[M-H]^-$, 440.

Examples 17 to 29

Examples 17 to 29, for which mass spectral data appear in the table below, were prepared by procedures analogous to those described for preparing Example 16 by coupling the requisite amine (usually as its hydrochloride salt, but including diisopropylethylamine in the reaction mixture regardless) with Example 7. Reaction times were typically 0.25–2 h, as necessary for complete reaction as determined by analytical HPLC/MS. The amines were commercially available unless otherwise noted. In the case of Example 20 and Example 23, the requisite amines, azetidine-3-carboxylic acid methyl ester (prepared from azetidine-3-carboxylic acid with chlorotrimethylsilane, methanol, heat) and glycine methyl ester hydrochloride, respectively, were used to prepare the methyl esters of Example 20 and Example 23, Example 19 and Example 22, respectively, and an additional step of ester hydrolysis (lithium hydroxide monohydrate, tetrahydrofuran, water) was performed prior to the reaction mixture being purified by reverse phase preparative HPLC (trifluoroacetic acid containing solvents were used) to obtain the final products. In the case of Example 24, the requisite amine, diethyl iminodiacetate, was used to prepare the diethyl ester of Example 24, and an additional step of ester hydrolysis, as set forth above, was performed prior to the reaction mixture being purified by reverse phase preparative HPLC (trifluoroacetic acid containing solvents were used) to obtain Example 24.

| Example | MS |
|---|---|
| 17 | $[M-H]^-$, 396 |
| 18 | $[M-H]^-$, 410 |
| 19 | $[M+H]^+$, 496 |
| 20 | $[M+H]^+$, 482 |
| 21 | $[M-H]^-$, 449 |
| 22 | $[M+H]^+$, 470 |
| 23 | $[M+Na]^+$, 478 |
| 24 | $[M+H]^+$, 514 |
| 25 | $[M-H]^-$, 480 |
| 26 | $[M-H]^-$, 624 |
| 27 | $[M+H]^+$, 489 |
| 28 | $[M-H]^-$, 488 |
| 29 | $[M-H]^-$, 473 |

Examples 30 to 34

Examples 30 to 34, for which mass spectral data appear in the table below, were prepared by procedures analogous to those described for Example 16 by coupling the requisite amine (usually as its hydrochloride salt, but including diisopropylethylamine in the reaction mixture regardless) with Example 9. The structure of Example 31 was confirmed by x-ray crystallography. The requisite amine for Example 32, 3-azetidinol hydrochloride, was prepared by hydrogenation of commercially available 1-benzhydrylazetidin-3-ol. The requisite amine for Example 33, cis-3,4-dihydroxypyrrolidine hydrochloride, was prepared in the manner disclosed in WO 96/39385.

| Example | MS |
|---|---|
| 30 | $[M - H]^-$, 424 |
| 31 | $[M - H]^-$, 440 |
| 32 | $[M - H]^-$, 452 |
| 33 | $[M - H]^-$, 482 |
| 34 | $[M - H]^-$, 480 |

Example 35

Example 35 was prepared from commercially available dimethylamine hydrochloride and Example 10 by a procedure analogous to the procedure described in Example 16. MS $[M-H]^-$, 424.

Example 36 and Example 37

Part I: Methyl esters of Example 36 and Example 37

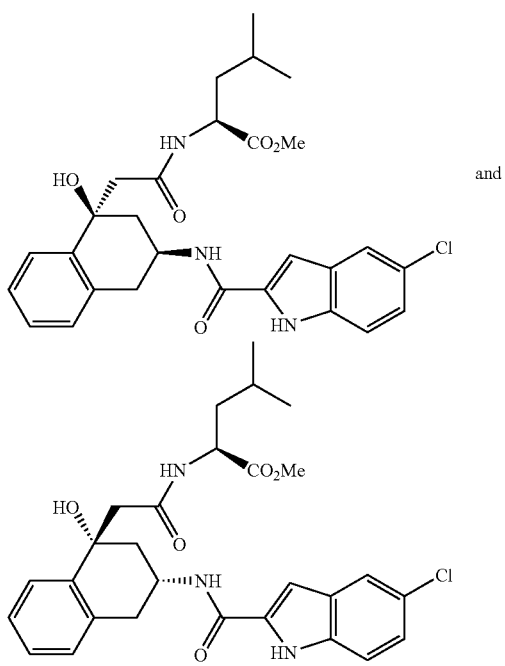

Example 7 (10 mg) and L-leucine methyl ester hydrochloride (excess) were coupled by a procedure analogous to the procedure described in Example 16 to yield crude product. The crude product was purified by reverse phase preparative HPLC (trifluoroacetic acid containing solvents were used) to obtain a 1:1 mixture of the methyl esters of Example 36 and Example 37.

Part II: Example 36 and Example 37

A 1:1 mixture of the methyl esters of Example 36 and Example 37 was dissolved in a mixture tetrahydrofuran and water (1:1) along with lithium hydroxide monohydrate (excess). The resulting solution was stirred for 2 h at room temperature under nitrogen. After this time, the tetrahydrofuran was removed under reduced pressure and the remaining aqueous solution was acidified to pH 1 with 1.0 M aqueous hydrochloric acid solution. The resulting mixture was extracted with ethyl acetate, and the organic layer was washed with brine, dried over anhydrous magnesium sulfate, and evaporated under vacuum to yield a residue. The residue was subjected to reverse phase preparative HPLC (trifluoroacetic acid containing solvents were used) to obtain Example 36 (eluted first, 3.9 mg) and Example 37 (eluted second, 4.2 mg). Both isomers MS [M+H]$^+$, 512. The absolute stereochemistry of the tetrahydronaphthalene stereocenters of these compounds was not determined.

Example 38

Example 7 (10 mg) and cis-4-hydroxy-L-proline methyl ester hydrochloride (excess) were coupled by a procedure analogous to the procedure described in Example 16 to yield crude product. The crude product was purified by reverse phase preparative HPLC (trifluoroacetic acid containing solvents were used) to obtain Example 38 (12 mg). MS [M−H]$^−$, 524.

Example 39

Example 38 (10 mg) was dissolved along with lithium hydroxide monohydrate (excess) in tetrahydrofuran and water (1:1). The resulting solution was stirred for 2 h under nitrogen at room temperature. After this time, the tetrahydrofuran was removed under reduced pressure and the remaining aqueous solution was acidified to pH 1 with 1.0 M aqueous hydrochloric acid solution. The resulting mixture was extracted with ethyl acetate, and the organic layer was washed with brine, dried over anhydrous magnesium sulfate, and evaporated under vacuum to yield a residue. The residue was subjected to reverse phase preparative HPLC (trifluoroacetic acid containing solvents were used) to obtain Example 39 (4.3 mg). MS [M−H]$^−$, 510.

Example 40

Example 40 was prepared in two steps from Example 7 and L-tyrosine methyl ester hydrochloride following procedures analogous to those used to prepare Example 39 from Example 7 via Example 38. MS [M−H]$^−$, 560.

Example 41

Part I: tert-Butyl (3R,5S)-6-(toluene-4-sulfonyloxy)-3,5-O-isopropylidene-3,5-dihydroxyhexanoate

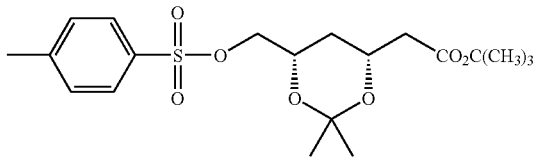

To a solution of tert-butyl (3R,5S)-6-hydroxy-3,5-O-isopropylidene-3,5-dihydroxyhexanoate (Kaneka Corporation, 200 mg) in pyridine (8 mL) stirring under nitrogen at room temperature was added p-toluenesulfonyl chloride (440 mg). After 1.5 h, the reaction mixture was diluted with ethyl acetate and washed sequentially with water, saturated aqueous sodium bicarbonate solution, and brine. The organic layer was dried over anhydrous magnesium sulfate, evaporated under vacuum and purified by silica gel chromatography (eluted with a step-wise 20–30% gradient of ethyl acetate in hexane) to obtain the title compound (264 mg) as a white solid.

Part II: tert-Butyl (3R,5S)-6-azido-3,5-O-isopropylidene-3,5-dihydroxyhexanoate

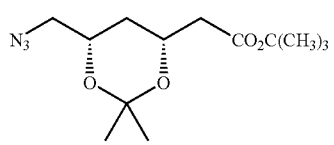

To a solution of tert-butyl (3R,5S)-6-(toluene-4-sulfonyloxy)-3,5-O-isopropylidene-3,5-dihydroxyhexanoate (264 mg) in N,N-dimethylformamide (3 mL) stirring under nitrogen was added sodium azide. Upon completion of addition, the reaction mixture was heated to 80° C. for 9 h. After cooling to room temperature, the reaction mixture was diluted with ethyl acetate and washed with 1.0 M aqueous hydrochloric acid solution until no N,N-dimethylformamide was detected in the organic layer by TLC analysis. The organic layer was dried over anhydrous magnesium sulfate and evaporated under vacuum to obtain the title compound (161 mg) as a clear oil.

Part III: tert-Butyl (3R,5S)-6-amino-3,5-O-isopropylidene-3,5-dihydroxyhexanoate

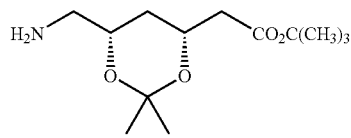

tert-Butyl (3R,5S)-6-azido-3,5-O-isopropylidene-3,5-dihydroxyhexanoate (161 mg) was dissolved in methanol (2 mL) containing 10% palladium on carbon (60 mg). The resulting mixture was stirred under a hydrogen balloon for 2 h at room temperature. After this time, the reaction mixture was filtered through Celite®. The filtercake was rinsed with methanol, and the filtrate was evaporated under vacuum to obtain the title compound (140 mg) as a pale yellow oil.

Part IV: Acetonide and t-butyl ester protected Example 41

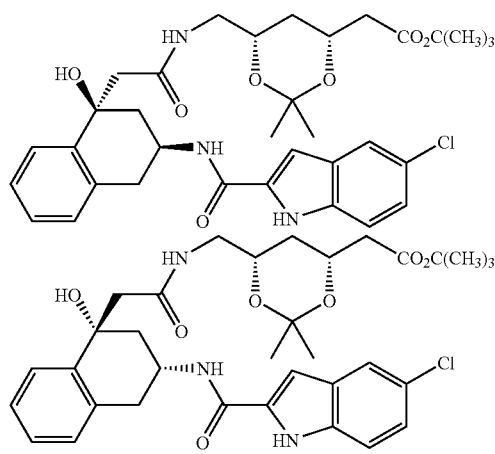

Example 7 (10 mg) and tert-butyl (3R,5S)-6-amino-3,5-O-isopropylidene-3,5-dihydroxyhexanoate (excess) were coupled by a procedure analogous to the procedure described in Example 16 to obtain the title compound (10 mg).

Part V: Example 41

To acetonide and t-butyl ester protected Example 41 (10 mg) was added water (0.5 mL) and trifluoroacetic acid (5 drops from a Pasteur pipette). Upon completion of addition, the reaction mixture was stirred for 2 h under nitrogen at room temperature, during which a white solid formed. The mixture was then extracted with ethyl acetate, and the extracts were washed sequentially with saturated aqueous sodium bicarbonate solution and brine, then dried over anhydrous magnesium sulfate and evaporated under vacuum to yield a residue. The residue was dissolved in methanol (2 mL) under nitrogen with stirring and lithium hydroxide monohydrate (excess) was added. The reaction mixture was heated to reflux for 30 min. At the conclusion of this period, the reaction mixture was filtered, evaporated under vacuum, and the resulting residue was redissolved in water. The resulting solution was purified by chromatography on SP207 Li resin (eluted with water, then 25–75% methanol in water in a step-wise gradient) to obtain Example 41 (6.8 mg) as the lithium salt. MS [M–H]⁻, 543. The SP207 Li resin was prepared from SP207 Na resin by exchanging Na for Li by stirring with 1.0 M aqueous lithium hydroxide solution for 15 min, and then washing with 1.0 M aqueous lithium hydroxide solution (five times) followed by water until the washes were neutral.

Example 42

Example 42, as the lithium salt, (15 mg) was prepared from Example 10 (14 mg) following procedures analogous to those used to prepare Example 41 from Example 7. MS [M–H]⁻, 543. The structure of Example 42 was confirmed by x-ray crystallography.

Example 43

Part I: 3-Benzyloxycarbonylamino-1-cyanomethylene-1,2,3,4-tetrahydronaphthalene

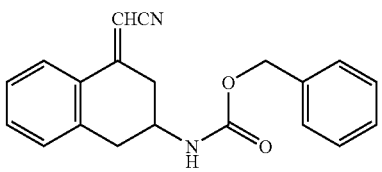

To a solution of diethyl (cyanomethyl)phosphonate (0.189 mL) in 1,2-dimethoxyethane (1 mL) at room temperature under nitrogen was added 60% sodium hydride oil dispersion (46 mg). Upon completion of addition, the mixture was stirred for 1 h. After this time, a solution of 3-benzyloxycarbonylamino-1-oxo-1,2,3,4-tetrahydronaphthalene (69 mg) in 1,2-dimethoxyethane was added (1 mL). The reaction mixture was stirred at room temperature for 1 h, and then heated to reflux for 4 h. At the conclusion of this period, the reaction mixture was cooled to room temperature, diluted with water, and then extracted with ethyl acetate. The organic layer was dried over anhydrous magnesium sulfate and evaporated under vacuum to yield a residue. The residue was purified by reverse phase preparative HPLC (trifluoroacetic acid containing solvents were used) to obtain the title compound (38 mg) as a mixture of olefin isomers.

Part II: 3-Amino-1-cyanomethyl-1,2,3,4-tetrahydronaphthalene, cis-trans mixture

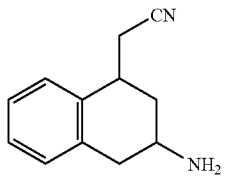

A mixture of 3-benzyloxycarbonylamino-1-cyanomethylene-1,2,3,4-tetrahydronaphthalene olefin isomers (24.7 mg) was dissolved in ethanol (2 mL) at room temperature and 10% palladium on carbon (10 mg) was added. Hydrogen gas was bubbled through this mixture for 10 min before it was stirred under a hydrogen balloon for 24 h. After this time, the reaction mixture was filtered through Celite® and the filtrate was evaporated under vacuum to obtain the title compound (9.9 mg).

Part III: Example 43

To a solution containing a cis-trans mixture of 3-amino-1-cyanomethyl-1,2,3,4-tetrahydronaphthalene (20.8 mg) in tetrahydrofuran (1 mL) was added diisopropylethylamine (0.038 mL), 1-(3-dimethylaminopropyl)-3-ethylcarbodiimide hydrochloride (43 mg), 1-hydroxy-7-azabenzotriazole (30 mg) and 5-chloroindole-2-carboxylic acid (24 mg). After stirring for 45 min at room temperature under nitrogen, the reaction mixture was diluted with ethyl acetate and then washed sequentially with 1.0 M aqueous hydrochloric acid solution, 1.0 M aqueous sodium hydroxide solution, and brine. The organic layer was dried over anhydrous magnesium sulfate and evaporated under vacuum to yield a residue. The residue was purified by reverse phase preparative HPLC (trifluoroacetic acid containing solvents were used) to obtain crude Example 43 contaminated with Example 44 (19.9 mg). The crude Example 43 (19.9 mg) was recrystallized from deuteriochloroform to obtain Example 43 (3.2 mg). The relative stereochemistry of Example 43 was determined by x-ray crystallography. MS [M−H]⁻, 362.

Example 44

Example 44 was prepared from trans-3-amino-1-cyanomethyl-1,2,3,4-tetrahydronaphthalene following a procedure analogous to the procedure described in Part III, Example 43, but omitting the final recrystallization. MS [M−H]⁻, 362. Trans-3-amino-1-cyanomethyl-1,2,3,4-tetrahydronaphthalene was obtained by separation of the cis-trans mixture prepared in Part II, Example 43 by reverse phase preparative HPLC (trifluoroacetic acid containing solvents were used, the trans isomer eluted before the cis isomer).

Example 45

Part I: 3-Benzyloxycarbonylamino-1-carboethoxymethylene-1,2,3,4-tetrahydronaphthalene

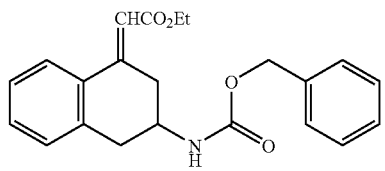

To a solution of triethyl phosphonoacetate (0.202 mL) in ethanol (2 mL) stirring at 0° C. under nitrogen was added a solution of sodium ethoxide in ethanol (21% by weight, 0.379 mL). After 1 h, a solution of 3-benzyloxycarbonylamino-1-oxo-1,2,3,4-tetrahydronaphthalene (100 mg) in ethanol (1 mL) was added. Upon completion of addition, the reaction mixture was stirred for 12 h and allowed to warm to room temperature. The reaction mixture was then quenched with 1.0 M aqueous hydrochloric acid solution and the ethanol was removed under reduced pressure. Water was added and the reaction mixture was extracted with ethyl acetate. The organic layer was dried over anhydrous magnesium sulfate and evaporated under vacuum to yield a residue. The residue was purified by reverse phase preparative HPLC (trifluoroacetic acid containing solvents were used) to obtain the title compound (55 mg) as a 2.7:1 mixture of the olefin isomers, which were separable but were combined for use in the next step.

Part II: 3-Amino-1-carboethoxymethyl-1,2,3,4-tetrahydronaphthalene, cis-trans mixture

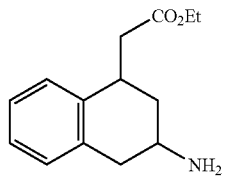

To a solution of 3-benzyloxycarbonylamino-1-carboethoxymethylene-1,2,3,4-tetrahydronaphthalene (2.7:1 stereoisomeric mixture, 55 mg) in ethanol (2 mL) stirring at room temperature was added 10% palladium on carbon (6 mg). The reaction mixture was hydrogenated (balloon) for 3 d. At the conclusion of this period, the reaction mixture was filtered through Celite® and evaporated under vacuum to obtain the title compound (30 mg) as a cis-trans mixture which was inseparable by HPLC.

Part III: Mixture of the Ethyl Ester of Example 45 and its Trans Isomer

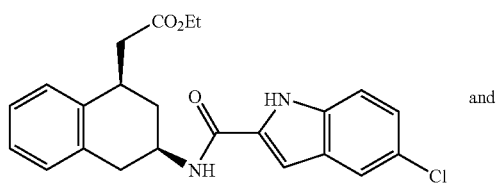

and

-continued

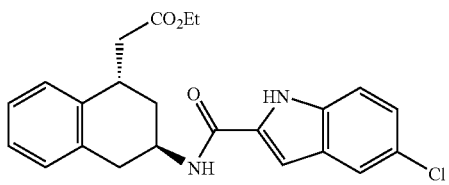

A cis-trans mixture of 3-amino-1-carboethoxymethyl-1,2,3,4-tetrahydronaphthalene (30 mg) was coupled with 5-chloroindole-2-carboxylic acid (28 mg) by a procedure analogous to the procedure described in Part III, Example 5 to yield crude product. The crude product was purified by reverse phase preparative HPLC (trifluoroacetic acid containing solvents were used) to obtain the title compound (25 mg).

Part IV: Example 45

To a solution of a mixture of the ethyl ester of Example 45 and its trans isomer (25 mg) in tetrahydrofuran and water (1:1) was added lithium hydroxide monohydrate (excess). After stirring for 16 h at room temperature under nitrogen, the reaction mixture was concentrated under vacuum, diluted with water, and acidified to pH 1 with 1.0 M aqueous hydrochloric acid solution. The resulting pink solid was collected by filtration to yield 27 mg of a 7:4 mixture of diastereomers. The pink solid was recrystallized from methanol/water to obtain Example 45 (4.7 mg) as a white solid. MS [M+H]+, 383. The relative stereochemistry was assigned by NOE experiments.

Example 46

Example 46 was prepared from racemic 3-carboxy-1-oxobenzocycloheptane (prepared in the manner disclosed in WO 00/27815 and T. W. Doyle, Can. J. Chem. 1971, 49, 1759–1762) following procedures analogous to those used to prepare Example 1 from 3-carboxy-1-oxo-1,2,3,4-tetrahydronaphthalene. MS [M−H]−, 391.

Example 47

Example 47 was prepared from racemic 3-carboxy-1-oxobenzocycloheptane following procedures analogous to those used to prepare Example 2 from 3-carboxy-1-oxo-1,2,3,4-tetrahydronaphthalene. MS [M−H]−, 391.

Example 48

Example 8 (2.7 mg) and ethyl-4-aminobenzoate (excess) were coupled by a procedure analogous to Example 16 to yield crude product. The crude product was purified by preparative reverse phase HPLC to obtain a mixture of an expected amide (2.2 mg) and Example 48 (1.0 mg). MS [M−H]−, 335.

Example 49

Part I:
Trans-4-benzyloxycarbonylaminocyclohexanol

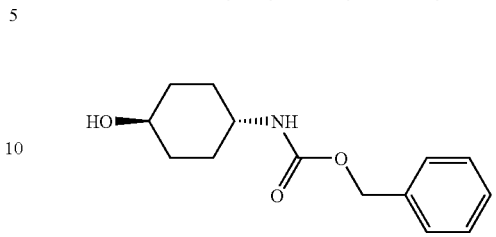

To a stirred solution of trans-4-aminocyclohexanol (35.5 g, 306.6 mmol) in methanol (621 mL) at 0° C. under nitrogen was added N-(benzyloxycarbonyloxy)succinimide (72.8 g, 291.9 mmol). The reaction mixture was slowly warmed to room temperature and after 1 d, poured into 0.25 M aqueous hydrochloric acid solution (2.13 L). The resulting slurry was stirred vigorously for 1 h and then filtered. The filtered solid was washed with water to obtain the title compound (65.65 g, 90%) as a white solid. $^{13}$C NMR (400 MHz, (CD$_3$)$_2$SO) δ 155.3, 137.2, 128.3, 127.7, 127.6, 68.1, 65.0, 49.1, 33.9, 30.3. $^1$H NMR (400 MHz, (CD$_3$)$_2$SO) δ 7.29 (m, 5H), 7.10 (d, J=7.9 Hz, 1H), 4.96 (d, J=2.3 Hz, 2H), 4.76 (d, J=4.0 Hz, 1H), 3.29 (s, 1H), 3.17 (br s, 1H), 1.71 (m, 4H), 1.22 (t, J=9.7 Hz, 4H).

Part II: 4-Benzyloxycarbonylaminocyclohexanone

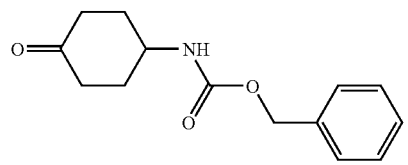

To a stirred solution of trans-4-benzyloxycarbonylaminocyclohexanol (21.5 g, 86.3 mmol) in acetic acid (160 mL) at room temperature under nitrogen was added chromium trioxide (8.63 g, 86.3 mmol). After 1 d, the reaction mixture was evaporated under vacuum to yield a residue. The residue was suspended in acetone and filtered through a plug of Celite®. The filtrate was evaporated to obtain a green solid. The green solid was purified by silica gel chromatography (eluted with 5% methanol in methylene chloride) to obtain the title compound (16.65 g, 78%) as an off-white solid. $^{13}$C NMR (400 MHz, CDCl$_3$) δ 209.6, 155.8, 136.2, 128.5, 128.2, 128.1, 66.8, 47.9, 38.8, 32.1. $^1$H NMR (400 MHz, CDCl$_3$) δ 7.34 (m, 5H), 5.09 (s, 2H), 4.84 (br s, 1H), 3.97 (s, 1H), 2.38 (m, 4H), 2.20 (m, 2H), 1.68 (m, 2H). HPLC/MS [M+H]+, 248.

Part III: 3-Aminoacrolein

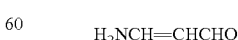

H$_2$NCH=CHCHO

In a pressure bottle, Raney Ni (50% slurry in water, 4.0 g, 34.1 mmol) was stirred three times in methanol and decanted. To this catalyst was added a solution of isoxazole (10.0 g, 144.8 mmol) in methanol (200 mL). Upon completion of addition, the reaction mixture was placed under a hydrogen atmosphere at 40 psi and shaken on a Parr appa- Part IV: 6-Benzyloxycarbonylamino-5,6,7,8-tetrahydroquinoline

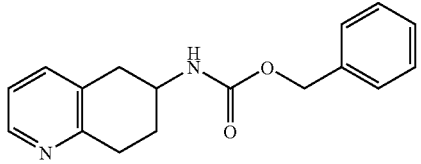

A mixture of 4-benzyloxycarbonylaminocyclohexanone (13.75 g, 55.6 mmol), 3-aminopropenal (5.57 g, 78.4 mmol), and ammonium acetate (0.14 g, 1.78 mmol) in triethylamine (85 mL) was stirred at 115° C. under nitrogen for 3 d. The reaction mixture was then partitioned between chloroform and water. The organic layer was separated, washed sequentially with water, saturated aqueous ammonium chloride solution and brine, dried over anhydrous magnesium sulfate, and evaporated under vacuum to yield a residue. The residue was subjected to silica gel chromatography (eluted with 5% methanol in methylene chloride) to obtain the title compound (1.67 g, 10.5%) as a brown oil. $^{3}$C NMR (400 MHz, CDCl$_3$) δ 155.6, 147.5, 137.2, 136.4, 129.2, 128.5, 128.1, 121.2, 66.7, 46.2, 35.2, 30.1, 28.7. $^1$H NMR (400 MHz, CDCl$_3$) δ 8.31 (d, J=4.4 Hz, 1H), 7.27 (m, 6H), 6.98 (dd, J=4.8, 7.5 Hz, 1H), 5.03 (s, 2H), 4.85 (br s, 1H), 4.00 (br s, 1H), 3.06 (d, J=16.3 Hz, 1H), 2.97 (t, J=6.6 Hz, 2H), 2.62 (dd, J=7.9, 16.0 Hz, 1H), 2.08 (d, J=8.4 Hz, 1H), 1.82 (m, 1H).

Part V: 6-Benzyloxycarbonylamino-5,6,7,8-tetrahydroquinoline 1-oxide

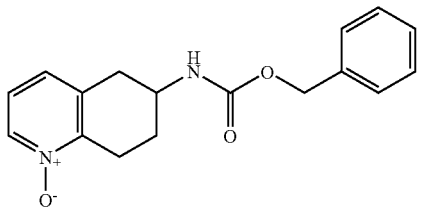

To a stirred solution of 6-benzyloxycarbonylamino-5,6,7,8-tetrahydroquinoline (1.66 g, 5.87 mmol) in chloroform (13 mL) at 0° C. under nitrogen was added 3-chloroperoxybenzoic acid (1.06 g net, 6.16 mmol). The reaction mixture was then slowly warmed to room temperature. After 1 d, the reaction mixture was chromatographed on basic alumina (eluted with a 0–3% step-wise gradient of methanol in methylene chloride). The title compound (1.16 g, 66.5%) was obtained as a light yellow solid. $^{13}$C NMR (400 MHz, CDCl$_3$) δ 155.7, 147.2, 137.3, 136.3, 133.5, 128.5, 128.1, 128.0, 126.5, 122.6, 66.8, 45.4, 36.7, 27.3, 22.9. $^1$H NMR (400 MHz, CDCl$_3$) δ 8.10 (d, J=6.2 Hz, 1H), 7.31 (m, 5H), 7.00 (m, 2H), 5.07 (s, 2H), 3.98 (br s, 1H), 3.12 (m, 2H), 2.95 (m, 1H), 2.70 (dd, J=7.9, 16.0 Hz, 1H), 2.11 (m, 1H), 1.86 (br s, 1H). HPLC/MS [M+H]$^+$, 299.

Part VI: 8-Acetoxy-6-benzyloxycarbonylamino-5,6,7,8-tetrahydroquinoline, cis-trans mixture

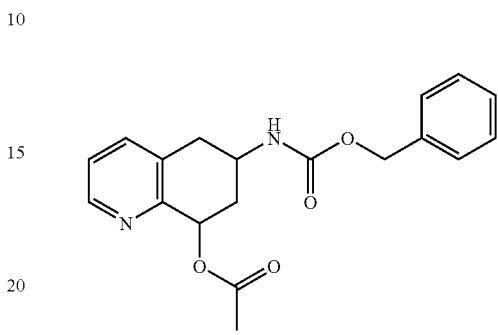

6-Benzyloxycarbonylamino-5,6,7,8-tetrahydroquinoline 1-oxide (1.62 g, 5.44 mmol) was dissolved in acetic anhydride (7.7 mL, 81.6 mmol), and the reaction mixture was stirred at 60° C. for 2 h under nitrogen. After this time, the solvent was removed under vacuum to yield a residue, which was dissolved in methylene chloride. The resulting solution was washed sequentially with water, saturated aqueous sodium carbonate solution and brine, dried over anhydrous magnesium sulfate, and evaporated under vacuum to obtain the title compound (1.73 g, 93%) as a brown oil. HPLC/MS [M+H]$^+$, 341.

Part VII: 6-Benzyloxycarbonylamino-8-hydroxy-5,6,7,8-tetrahydroquinoline, cis-trans mixture

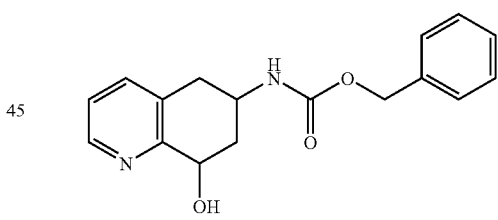

To a stirred solution of 8-acetoxy-6-benzyloxycarbonylamino-5,6,7,8-tetrahydroquinoline, cis-trans mixture (1.73 g, 5.07 mmol) in methanol (16 mL) at room temperature under nitrogen was added 10% aqueous potassium carbonate solution (8 mL, 5.79 mmol). After 24 h, the reaction mixture was diluted with methylene chloride. The organic layer was washed sequentially with saturated aqueous ammonium chloride solution and brine, dried over anhydrous magnesium sulfate, and evaporated under vacuum to obtain the title compound (1.47 g, 97%). Silica gel chromatography (eluted with 5% methanol in chloroform) provided inefficient separation of the cis and trans isomers. The cis isomer eluted first. Stereochemical assignment was made based on NOE experiments. Cis isomer: $^{13}$C NMR (400 MHz, CDCl$_3$) δ 156.3, 155.8, 147.5, 138.0, 136.5, 128.5, 128.1, 123.1, 77.4, 67.5, 66.5, 44.4, 35.0. HPLC/MS [M+H]$^+$, 299.

ratus for 24 h. At the conclusion of this period, the reaction mixture was filtered through Celite®, rinsing the catalyst with methanol. The filtrate was evaporated under vacuum to obtain the title compound (9.2 g, 94%) as an orange-brown solid. $^{13}$C NMR (400 MHz, CD$_3$OD) δ 192.3, 163.8, 104.3. $^1$H NMR (400 MHz, CD$_3$OD) δ 8.82 (d, J=9.2 Hz, 1H), 7.41 (d, J=12.8 Hz, 1H), 5.37 (dd, J=9.2, 12.8 Hz, 1H). Elemental analysis calculated: C 50.69%, H 7.09%, and N 19.70%. Found: C 50.75%, H 6.96%, and N 18.79%.

Part VIII: 6-Benzyloxycarbonylamino-8-oxo-5,6,7,8-tetrahydroquinoline

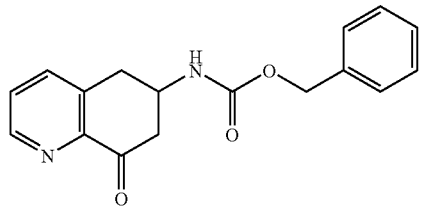

To a stirred solution of 6-benzyloxycarbonylamino-8-hydroxy-5,6,7,8-tetrahydroquinoline, cis-trans mixture (1.02 g, 3.42 mmol) in methylene chloride (34 mL) at room temperature under nitrogen was added Dess-Martin periodinane (1.73 g, 4.45 mmol). After 2 h, the reaction mixture was diluted with ethyl acetate. The organic layer was washed sequentially with saturated aqueous sodium bicarbonate solution and brine, dried over anhydrous magnesium sulfate, and evaporated under vacuum to yield a residue. The residue was purified by reverse phase preparative HPLC to obtain the title compound (319 mg, 31%) as a brown oil. $^{13}$C NMR (400 MHz, CDCl$_3$) δ 194.1, 155.4, 149.8, 147.6, 138.3, 137.2, 136.0, 128.6, 128.3, 128.2, 127.5, 67.0, 46.7, 45.4, 35.4. $^1$H NMR (400 MHz, CDCl$_3$) δ 8.66 (d, J=4.4 Hz, 1H), 7.61 (d, J=7.9 Hz, 1H), 7.36 (dd, J=4.4, 7.9 Hz, 1H), 7.26 (m, 5H), 5.02 (s, 2H), 4.34 (s, 1H), 3.29 (d, J=15.4 Hz, 1H), 3.04 (d, J=4.0 Hz, 1H), 2.99 (d, J=4.0 Hz, 1H), 2.80 (dd, J=9.2, 11.4 Hz, 1H). HPLC/MS [M+H]$^+$, 297.

Part IX: (R/S)-(6R*,8S*)-6-benzyloxycarbonylamino-8-hydroxy-8-phenylsulfonylmethyl-5,6,7,8-tetrahydroquinoline and (R/S)-(6R*,8R*)-6-benzyloxycarbonylamino-8-hydroxy-8-phenylsulfonylmethyl-5,6,7,8-tetrahydroquinoline

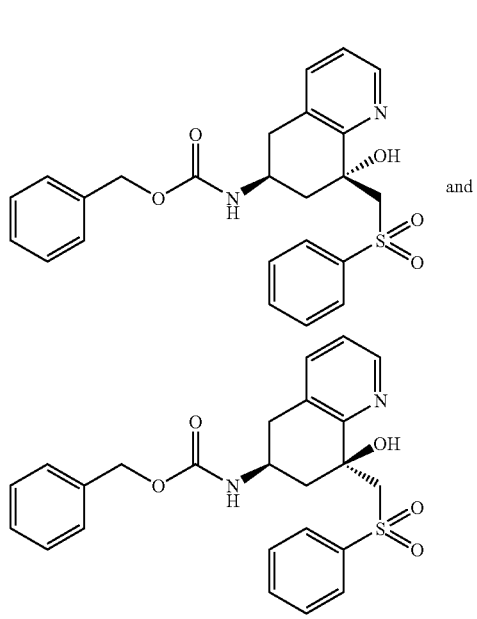

To a stirred solution of methyl phenyl sulfone (264 mg, 1.68 mmol) in tetrahydrofuran (10 mL) at −78° C. under nitrogen was added lithium hexamethyldisilazide (1.7 mL, 1.68 mmol) dropwise. After 1 h, a solution of 6-benzyloxycarbonylamino-8-oxo-5,6,7,8-tetrahydroquinoline (100 mg, 0.337 mmol) and lithium bromide (87.9 mg, 1.012 mmol) in tetrahydrofuran (1 mL) at room temperature under nitrogen was added slowly to the cold solution. The reaction mixture was quenched with saturated aqueous ammonium chloride solution 1 h later and diluted with ethyl acetate. The organic layer was separated and washed sequentially with 1.0 M aqueous hydrochloric acid solution, 1.0 M aqueous sodium hydroxide solution and brine, dried over anhydrous magnesium sulfate, and evaporated under vacuum to yield a residue. The residue was purified by reverse phase preparative HPLC to obtain (R/S)-(6R*,8S*)-6-benzyloxycarbonylamino-8-hydroxy-8-phenylsulfonylmethyl-5,6,7,8-tetrahydroquinoline (54.3 mg, 36%) and (R/S)-(6R*,8R*)-6-benzyloxycarbonylamino-8-hydroxy-8-phenylsulfonylmethyl-5,6,7,8-tetrahydroquinoline (20 mg, 13%), both as light yellow oils, in addition to mixed fractions and recovered starting material. The relative stereochemistry of the (R/S)-(6R*,8S*) product was determined by NOE experiments. (R/S)-(6R*,8S*) product: $^1$H NMR (400 MHz, CDCl$_3$) δ 8.18 (d, J=4.4 Hz, 1H), 7.69 (d, J=7.5 Hz, 2H), 7.51 (d, J=5.8 Hz, 1H), 7.21–7.43 (m, 8H), 7.01 (dd, J=4.8, 7.9 Hz, 1H), 5.06 (s, 2H), 4.95 (d, J=5.7 Hz, 1H), 4.15 (m, 1H), 4.03 (d, J=14.1 Hz, 1H), 3.78 (d, J=14.0 Hz, 1H), 3.14 (d, J=11.8 Hz, 1H), 2.66 (m, 2H), 2.48 (t, J=12.8 Hz, 1H). HPLC/MS [M+H]$^+$, 453. (R/S)-(6R*,8R*) product: $^1$H NMR (400 MHz, CDCl$_3$) δ 8.16 (d, J=4.0 Hz, 1H), 7.70 (d, J=7.5 Hz, 2H), 7.52 (d, J=7.5 Hz, 1H), 7.22–7.47 (m, 8H), 7.04 (dd, J=4.8, 8.0 Hz, 1H), 6.13 (d, J=6.6 Hz, 1H), 5.05 (d, J=12.3 Hz, 1H), 4.96 (d, J=12.3 Hz, 1H), 4.29 (m, 1H), 3.98 (d, J=14.0 Hz, 1H), 3.81 (d, J=14.0 Hz, 1H), 3.04 (m, 2H), 2.86 (dd, J=3.1, 14.5 Hz, 1H), 2.60 (dd, J=4.0, 14.5 Hz, 1H). HPLC/MS [M+H]$^+$, 453.

Part X: (R/S)-(6R*,8S*)-6-amino-8-hydroxy-8-phenylsulfonylmethyl-5,6,7,8-tetrahydroquinoline

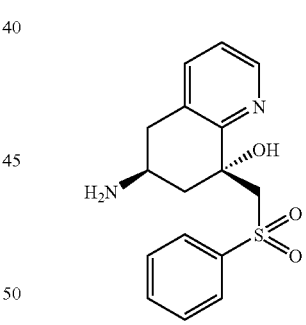

To a stirred solution of (R/S)-(6R*,8S*)-6-benzyloxycarbonylamino-8-hydroxy-8-phenylsulfonylmethyl-5,6,7,8-tetrahydroquinoline (54.3 mg, 0.12 mmol) in methanol (3 mL) was added 10% palladium on carbon (12.8 mg). The reaction mixture was placed under a hydrogen balloon at room temperature for 16 h then filtered through a plug of Celite®. The filtrate was evaporated under vacuum to obtain the title compound (38.6 mg, 100%) as a light yellow oil.

Part XI: Example 49

To a stirred solution of (R/S)-(6R*,8S*)-6-amino-8-hydroxy-8-phenylsulfonylmethyl-5,6,7,8-tetrahydroquinoline (38.6 mg, 0.121 mmol) and 5-chloroindole-2-carboxylic acid (26 mg, 0.133 mmol) in tetrahydrofuran (1.5 mL) and N,N-dimethylformamide (0.3 mL) at room temperature under nitrogen was added 1-[3-dimethylamino)propyl]-3-ethylcarbodiimide hydrochloride (46.4 mg, 0.242 mmol), 1-hydroxy-7-azabenzotriazole (33.1 mg, 0.242 mmol), and diisopropylethylamine (31.3 mg, 0.242 mmol). After 3 h, the reaction mixture was diluted with ethyl acetate. The organic layer was washed sequentially with 1.0 M aqueous hydrochloric acid solution, 1.0 M aqueous sodium hydroxide solution and brine, dried over anhydrous magnesium sulfate, and evaporated to yield a residue. The residue was purified by reverse phase preparative HPLC (trifluoroacetic acid containing solvents were used) to obtain Example 49 (41.4 mg, 68%) as a white solid. $^1$H NMR (500 MHz, d$_8$-tetrahydrofuran) δ 11.13 (s, 1H), 10.85 (s, 1H), 8.28 (d, J=3.8 Hz, 1H), 8.21 (d, J=2.2 Hz, 1H), 7.78 (d, J=6.8 Hz, 2H), 7.54 (t, J=6.4 Hz, 1H), 7.47 (m, 4H), 7.34 (d, J=7.6 Hz, 1H), 7.10 (m, 2H), 4.60 (br s, 1H), 4.17 (d, J=14.0 Hz, 1H), 3.94 (d, J=14.0 Hz, 1H), 3.14 (m, 2H), 3.02 (d, J=12.6 Hz, 1H), 2.53 (m, 1H). HPLC/MS [M+Na]$^+$, 520.

Example 50

Part I: (R/S)-(6R*,8R*)-6-amino-8-hydroxy-8-phenylsulfonylmethyl-5,6,7,8-tetrahydroquinoline, trifluoroacetic acid salt

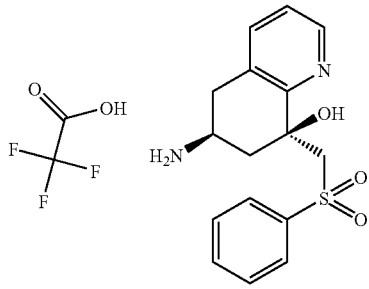

To a stirred solution of (R/S)-(6R*,8R*)-6-benzyloxycarbonylamino-8-hydroxy-8-phenylsulfonylmethyl-5,6,7,8-tetrahydroquinoline (20 mg, 0.044 mmol) in methanol (1 mL) at room temperature was added 10% palladium on carbon (4.7 mg). The reaction mixture was placed under a hydrogen balloon for 16 h. After this time, the reaction mixture was filtered through a plug of Celite® and evaporated under vacuum to yield a residue. The residue was purified by reverse phase preparative HPLC (trifluoroacetic acid containing solvents were used) to obtain the title compound (5.5 mg, 39%) as a light yellow oil. $^1$H NMR (500 MHz, d$_8$-tetrahydrofuran) δ 8.17 (d, J=4.4 Hz, 1H), 7.76 (dd, J=2.2, 7.5 Hz, 2H), 7.53 (t, J=7.6 Hz, 1H), 7.46 (t, J=7.6 Hz, 2H), 7.42 (d, J=8.0 Hz, 1H), 7.04 (dd, J=4.4, 6.2 Hz, 1H), 4.16 (d, J=14.2 Hz, 1H), 3.92 (d, J=14.2 Hz, 1H), 3.42 (m, 2H), 2.96 (d, J=14.4 Hz, 1H), 2.63 (m, 1H), 2.42 (m, 1H). HPLC/MS [M+H]$^+$, 319.

Part II: Example 50

To a stirred solution of (R/S)-(6R*,8R*)-6-amino-8-hydroxy-8-phenylsulfonylmethyl-5,6,7,8-tetrahydroquinoline, trifluoroacetic acid salt (5.5 mg, 0.017 mmol) and 5-chloroindole-2-carboxylic acid (3.7 mg, 0.019 mmol) in tetrahydrofuran (0.4 mL) at room temperature under nitrogen was added 1-[3-dimethylamino)propyl]-3-ethylcarbodiimide hydrochloride (6.6 mg, 0.035 mmol), 1-hydroxy-7-azabenzotriazole (4.7 mg, 0.035 mmol), and diisopropylethylamine (4.5 mg, 0.035 mmol). After 16 h, the reaction mixture was diluted with ethyl acetate. The organic layer was washed sequentially with 1.0 M aqueous hydrochloric acid solution, 1.0 M aqueous sodium hydroxide solution, and brine, dried over anhydrous magnesium sulfate, and evaporated to yield a residue. The residue was purified by reverse phase preparative HPLC (trifluoroacetic acid containing solvents were used) to obtain Example 50 (3.8 mg, 44%) as a white solid. $^1$H NMR (500 MHz, d$_8$-tetrahydrofuran) δ 11.18 (s, 1H), 10.85 (s, 1H), 8.21 (d, J=2.5 Hz, 1H), 7.98 (d, J=7.5 Hz, 1H), 7.43 (d, J=8.0 Hz, 2H), 7.61 (d, J=1.7 Hz, 1H), 7.57 (t, J=7.6 Hz, 1H), 746 (t, J=8.0 Hz, 3H), 7.42 (d, J=8.2 Hz, 1H), 7.15 (dd, J=1.8, 7.6 Hz, 1H), 7.08 (dd, J=4.4, 7.8 Hz, 1H), 7.03 (s, 1H), 4.66 (m, 1H), 4.35 (d, J=14.4 Hz, 1H), 3.84 (d, J=14.4 Hz, 1H), 3.22 (d, J=15.6 Hz, 1H), 2.80 (m, 2H), 2.55 (m, 1H). HPLC/MS [M+H]$^+$, 498.

Example 51

Part I: (R/S)-(6R*,8S*)-6-benzyloxycarbonylamino-8-carboethoxymethyl-8-hydroxy-5,6,7,8-tetrahydroquinoline

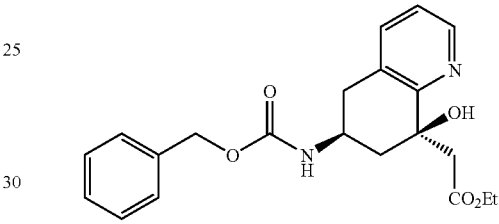

To a solution of lithium hexamethyldisilazide in tetrahydrofuran (2.13 mL of 1.0 M reagent in tetrahydrofuran solution was diluted with 2.1 mL tetrahydrofuran) stirring at −78° C. under nitrogen was added ethyl acetate (0.21 mL). This was stirred for 1 h at −78° C. before a solution of 6-benzyloxycarbonylamino-8-oxo-5,6,7,8-tetrahydroquinoline (126 mg) dissolved in tetrahydrofuran (2.1 mL) with lithium bromide (0.11 g) was added. After the combined solution was stirred at −78° C. for 1.5 h, the reaction mixture was quenched with saturated aqueous ammonium chloride solution. Ethyl acetate was added and the layers were separated. The organic layer was washed with brine, dried over anhydrous magnesium sulfate, and evaporated under vacuum to yield a residue. The residue was purified by reverse phase preparative HPLC (trifluoroacetic acid containing solvents were used) to obtain the title compound (111 mg) as the only identified isomer.

Part II: (R/S)-(6R*,8S*)-6-amino-8-carboethoxymethyl-8-hydroxy-5,6,7,8-tetrahydroquinoline

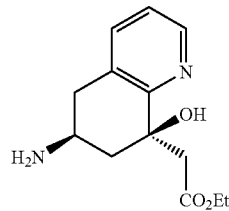

(R/S)-(6R*,8S*)-6-benzyloxycarbonylamino-8-carboethoxymethyl-8-hydroxy-5,6,7,8-tetrahydroquinoline (111 mg) was dissolved in ethanol (3 mL) with stirring at room temperature. Upon dissolution, 10% palladium on carbon (31 mg) was added. The reaction mixture was hydrogenated under a hydrogen balloon for 16 h. After this time, the reaction mixture was filtered through Celite® and evaporated under vacuum to obtain the title compound (80 mg).

Part III: Example 51

(R/S)-(6R*,8S*)-6-amino-8-carboethoxymethyl-8-hydroxy-5,6,7,8-tetrahydroquinoline (80 mg) and 5-chloroindole-2-carboxylic acid were coupled by a procedure analogous to the procedure described in Part III, Example 5 to yield crude product. The crude product was purified by reverse phase preparative HPLC purification (trifluoroacetic acid containing solvents were used) to obtain Example 51 (59 mg). MS [M–H]⁻, 426.

What is claimed is:

1. A compound of the formula I

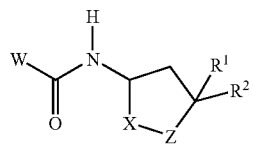

I or stereoisomers or prodrugs or pharmaceutically acceptable salts thereof, wherein $R^1$ is substituted alkyl or $OR^{7A}$; $R^2$ is substituted alkyl, $OR^{7A}$ $OCONR^{7A}R^{7B}$, CN, tetrazole substituted $R^{7A}$, $CO_2R^{7A}$, $CONR^{7A}R^{7B}$ or $NR^{7A}COCO_2R^{7B}$;

$R^{7A}$ and $R^{7B}$ are hydrogen or alkyl;
X is —CH₂— or —CH₂CH₂—;
W is

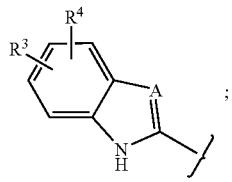

A is —CH—;
Z is

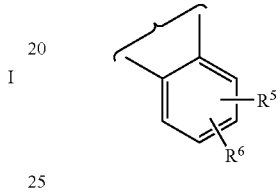

$R^3$ and $R^4$ are each independently hydrogen, halo, trifluoromethyl, cyano, alkyl or alkoxy; and
$R^5$ and $R^6$ are each independently hydrogen, halo, trifluoromethyl, cyano, hydroxy, alkyl, aryl, arylalkyl, heteroarylalkyl, alkoxy, aryloxy or alkenyl.

2. A compound of Table 1, wherein Table 1 is as follows:

TABLE 1

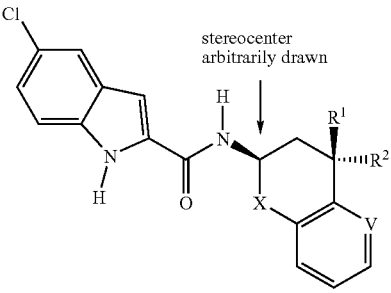

| Example | X | V | $R^1$ | $R^2$ | Stereochem. at center indicated |
|---|---|---|---|---|---|
| 1 | CH₂ | CH | OH | CH₂CN | R/S |
| 2 | CH₂ | CH | CH₂CN | OH | R/S |
| 3 | CH₂ | CH | OH | CH₂CN | homochiral as drawn |
| 4 | CH₂ | CH | OH | CH₂CN | homochiral opposite as drawn |
| 5 | CH₂ | CH | OH | CH₂CO₂Et | R/S |
| 6 | CH₂ | CH | CH₂CO₂Et | OH | R/S |
| 7 | CH₂ | CH | OH | CH₂CO₂H | R/S |
| 8 | CH₂ | CH | CH₂CO₂H | OH | R/S |
| 9 | CH₂ | CH | OH | CH₂CO₂H | homochiral as drawn |
| 10 | CH₂ | CH | OH | CH₂CO₂H | homochiral opposite as drawn |

TABLE 1-continued

| | | | | | |
|---|---|---|---|---|---|
| 11 | CH₂ | CH | OH | H₂C—[5-methyl-2H-tetrazole] | R/S |
| 12 | CH₂ | CH | OH | CH₂SO₂Me | R/S |
| 13 | CH₂ | CH | OH | CH₂SO₂C₆H₅ | R/S |
| 14 | CH₂ | CH | OH | CH₂SO₂C₆H₄-4-OH | R/S |
| 15 | CH₂ | CH | OH | CH₂C₆H₅ | R/S |
| 16 | CH₂ | CH | OH | CH₂CON(OMe)Me | R/S |
| 17 | CH₂ | CH | OH | CH₂CONH₂ | R/S |
| 18 | CH₂ | CH | OH | CH₂CONHMe | R/S |
| 19 | CH₂ | CH | OH | H₂C—C(O)—N-azetidine-3-CO₂Me | R/S |
| 20 | CH₂ | CH | OH | H₂C—C(O)—N-azetidine-3-CO₂H | R/S |
| 21 | CH₂ | CH | OH | CH₂CON(Me)CH₂CN | R/S |
| 22 | CH₂ | CH | OH | CH₂CONHCH₂CO₂Me | R/S |
| 23 | CH₂ | CH | OH | CH₂CONHCH₂CO₂H | R/S |
| 24 | CH₂ | CH | OH | CH₂CON(CH₂CO₂H)₂ | R/S |
| 25 | CH₂ | CH | OH | H₂C—C(O)—N-piperidine-4-OH | R/S |
| 26 | CH₂ | CH | OH | H₂C—C(O)—N-piperidine-4-(Ph-4-CF₃)-4-OH | R/S |
| 27 | CH₂ | CH | OH | H₂C—C(O)—NH—CH₂-(3-pyridyl) | R/S |
| 28 | CH₂ | CH | OH | CH₂CONHC₆H₄-4-OH | R/S |
| 29 | CH₂ | CH | OH | H₂C—C(O)—NH-(3-pyridyl) | R/S |
| 30 | CH₂ | CH | OH | CH₂CONMe₂ | homochiral as drawn |
| 31 | CH₂ | CH | OH | CH₂CON(OMe)Me | homochiral as drawn |
| 32 | CH₂ | CH | OH | H₂C—C(O)—N-azetidine-3-OH | homochiral as drawn |

TABLE 1-continued

| 33 | CH$_2$ | CH | OH | ![structure: acetyl pyrrolidine with two OH groups (trans-3,4-diol)] | homochiral as drawn |
| 34 | CH$_2$ | CH | OH | ![structure: acetyl piperidine with 3-OH] | homochiral as drawn |
| 35 | CH$_2$ | CH | OH | CH$_2$CONMe$_2$ | homochiral opposite as drawn |
| 36 | CH$_2$ | CH | OH | ![structure: N-acetyl leucine (S)] | homochiral unknown |
| 37 | CH$_2$ | CH | OH | ![structure: N-acetyl leucine (S)] | homochiral opposite Example 36 |
| 38 | CH$_2$ | CH | OH | ![structure: acetyl pyrrolidine with (R)-OH, (S)-CO$_2$Me] | R/S |
| 39 | CH$_2$ | CH | OH | ![structure: acetyl pyrrolidine with (R)-OH, (S)-CO$_2$H] | R/S |
| 40 | CH$_2$ | CH | OH | ![structure: N-acetyl tyrosine (S)] | R/S |
| 41 Lithium Salt | CH$_2$ | CH | OH | ![structure: acetamido diol diacid (S,R)] | R/S |
| 42 Lithium Salt | CH$_2$ | CH | OH | ![structure: acetamido diol diacid (S,R)] | homochiral opposite as drawn |
| 43 | CH$_2$ | CH | CH$_2$CN | H | R/S |

TABLE 1-continued

| 44 | CH$_2$ | CH | H | CH$_2$CN | R/S |
| --- | --- | --- | --- | --- | --- |
| 45 | CH$_2$ | CH | CH$_2$CO$_2$H | H | R/S |
| 46 | CH$_2$CH$_2$ | CH | OH | CH$_2$CN | R/S |
| 47 | CH$_2$CH$_2$ | CH | CH$_2$CN | OH | R/S |
| 48 | CH$_2$ | CH | together CH$_2$ | | R/S |
| 49 | CH$_2$ | N | CH$_2$SO$_2$C$_6$H$_5$ | OH | R/S |
| 50 | CH$_2$ | N | OH | CH$_2$SO$_2$C$_6$H$_5$ | R/S |
| 51 | CH$_2$ | N | OH | CH$_2$CO$_2$Et | R/S |

3. A pharmaceutical composition comprising a compound of claim 2 and a pharmaceutically acceptable carrier.

4. The compound of claim 1 wherein W is 5-chloroindol-2-yl.

5. The pharmaceutical composition of claim 3 further comprising at least one additional therapeutic agent.

6. A pharmaceutical composition comprising a compound of claim 1 and a pharmaceutically acceptable carrier.

7. The pharmaceutical composition of claim 6 further comprising at least one additional therapeutic agent.

* * * * *